(12) United States Patent
Byrne et al.

(10) Patent No.: US 12,300,382 B2
(45) Date of Patent: May 13, 2025

(54) DISINFECTION TRACKING NETWORK

(71) Applicant: UV Partners, Inc., Grand Haven, MI (US)

(72) Inventors: Paul Byrne, Washington, DC (US); David W Baarman, Fennville, MI (US); Luke Platz, Austin, TX (US); Colin J. Moore, Grand Rapids, MI (US)

(73) Assignee: UV Partners, Inc., Grand Haven, MI (US)

( * ) Notice: Subject to any disclaimer, the term of this patent is extended or adjusted under 35 U.S.C. 154(b) by 0 days.

(21) Appl. No.: 18/605,036

(22) Filed: Mar. 14, 2024

(65) Prior Publication Data

US 2024/0321438 A1  Sep. 26, 2024

Related U.S. Application Data

(63) Continuation of application No. 17/910,537, filed as application No. PCT/US2021/021629 on Mar. 10, 2021, now Pat. No. 11,961,614.

(60) Provisional application No. 62/988,181, filed on Mar. 11, 2020.

(51) Int. Cl.
*G16H 40/20* (2018.01)
*A61L 2/24* (2006.01)

(52) U.S. Cl.
CPC ............... *G16H 40/20* (2018.01); *A61L 2/24* (2013.01); *A61L 2202/14* (2013.01)

(58) Field of Classification Search
CPC ........ G16H 10/65; G16H 10/20; G16H 40/20; G16H 50/30; G16H 50/80; Y02A 90/10; A61L 2209/11; A61L 2202/14; A61L 2/24
See application file for complete search history.

(56) References Cited

U.S. PATENT DOCUMENTS

| | | | |
|---|---|---|---|
| 3,984,726 A | 10/1976 | Ramler | |
| 8,875,284 B1 * | 10/2014 | Newstadt | H04L 63/145 |
| | | | 726/22 |
| 10,198,779 B2 * | 2/2019 | Pittman | G16H 50/80 |
| 2010/0042394 A1 | 2/2010 | Khan | |
| 2010/0136586 A1 | 6/2010 | Caufield et al. | |
| 2012/0199003 A1 | 8/2012 | Melikov et al. | |
| 2013/0115132 A1 | 5/2013 | Engimann | |
| 2013/0183749 A1 | 7/2013 | Aamodt et al. | |

(Continued)

OTHER PUBLICATIONS

National Institute of Standards and Technology, U.S. Department of Commerce, "What is exerpimental design?" downloaded at https://www.itl.nist.gov/div898/handbook/pri/section1/pri11.htm on Mar. 5, 2020, pp. 1-3.

(Continued)

*Primary Examiner* — Etienne P Leroux
(74) *Attorney, Agent, or Firm* — Warner Norcross + Judd LLP

(57) ABSTRACT

A disinfecting tracking network for creating healthier environments. The system and methods for tracking and utilizing this information to build and maintain healthier environments with a laboratory approach to data inputs. This system is a cloud based system with IOT interface and APIs to enable broad reaching inputs for analysis. This system creates a safer ecosystem and cross statistic sharing of performance parameters.

20 Claims, 24 Drawing Sheets

(56) References Cited

U.S. PATENT DOCUMENTS

| | | | |
|---|---|---|---|
| 2014/0167917 A2* | 6/2014 | Wallace | G16H 40/67 340/10.1 |
| 2016/0008499 A1 | 1/2016 | Sunkara et al. | |
| 2016/0212577 A1 | 7/2016 | Dor et al. | |
| 2016/0306934 A1 | 10/2016 | Sperry et al. | |
| 2017/0322682 A1 | 11/2017 | Humayun et al. | |
| 2018/0000428 A1* | 1/2018 | Swiston | A61B 5/02055 |
| 2018/0144103 A1 | 5/2018 | Chae et al. | |
| 2018/0366221 A1 | 12/2018 | Crehore et al. | |
| 2018/0369438 A1 | 12/2018 | Grossman et al. | |
| 2019/0318815 A1 | 10/2019 | Bandurski et al. | |
| 2019/0365165 A1 | 12/2019 | Cawthon et al. | |
| 2020/0273562 A1 | 8/2020 | Tolbert | |
| 2022/0001050 A1 | 1/2022 | Terkelsen | |

OTHER PUBLICATIONS

Osterholm et al., "The Ebola Vaccine Team B: a model for promoting the rapid development of medical countermeasures for emerging infectious disease threats", Lancet Infectious Diseases, vol. 16, Jan. 2016, pp. e1-e9.

International Search Report and the Written Opinion of the International Searching Authority for International Application No. PCT/US2021/021629 mailed Aug. 9, 2021, pp. 1-13.

* cited by examiner

Disinfection Network Matrix

| | | EMR DATA | IOT DATA | ASSET TRACKING | CLINICAL SWABBING & MEASUREMENT | HAND WASHING | ROOM HISTORY | HOSPITAL HISTORY | HOSPITAL FINES | HOSPITAL PERFORMANCE | SURFACE MATERIALS | TERMINAL CLEANING | AIR DISINFECTION | CLEANING SERVICE | EMPLOYEE TRACKING | TOUCH TRACKING |
|---|---|---|---|---|---|---|---|---|---|---|---|---|---|---|---|---|
| 1 | Policies | x | x | x | x | x | | | | | | x | | x | x | x |
| 2 | Process | x | x | x | | x | | | | | | x | | x | x | x |
| 3 | Tracking | x | x | x | | x | | | | | | x | | | x | x |
| 4 | Measurement | | x | x | x | x | | | | | | | | | x | x |
| 5 | Tools | x | x | x | | | | | | | | x | | | | x |
| 6 | Mitigation | | x | x | | | | | | | | x | | | | x |
| 7 | Protocol | | x | x | | | | | | | | x | | | | x |
| 8 | Maintenance | | x | x | | | | | | | | x | x | x | | |
| 9 | Ext. Reports | | | | | | | | | | | | | | | |
| 10 | Ext. Data Services | | | | | | | x | x | x | | | | | | |
| 11 | Int. Data | | | | | | x | x | x | x | | | | | | |
| 12 | Configurations | x | x | x | | x | | | | | x | | | x | x | x |
| 13 | Behavior | x | x | x | x | x | x | | | | x | x | x | x | x | x |

Fig. 10

| Data | Terminal System | Hand-washing System #1 | Hand-washing System #2 | Hand-washing System #3 | Optical Recognition of Surface Contamination | Janitorial and Occupancy + IOT + Machine Learning System | Task System | Facilities Control System | Healthcare System | Biological System | Weather Service | Policy Cleaning |
|---|---|---|---|---|---|---|---|---|---|---|---|---|
| Terminal Cleaning Data | Yes | | | | | | | | | | | |
| Asset + People Tracking Data | | | | | | | | | | | | |
| Location data by asset | | Yes | | | | | | | | | | |
| Room by Room (threshold) | | Yes | | | | | | | | | | |
| Coordinates? | | Yes | | | | | | | | | | |
| Location data by Nurse | | Yes | | | | | | | | | | |
| Room by Room (threshold) Coordinates | | | | | | | | | | | | |
| Hand Washing Data | | | | | | | | | | | | |
| Time and location of Handwashing Execution | | Yes | Yes | Yes | | | | | | | | |
| Employee, Time, Location of Handwashing | | Yes | Yes | Yes | | | | | | | | |
| Dispensor Fill Levels (possibly just alert when low) | | Yes | Yes | Yes | | | | | | | | |
| Environmental Sensing Data | | Yes | | | | | | Yes | | | | |
| Surface Bioburden Data | | | | | | | | | | | | |
| CFU per surface | | | | | Yes | | | | | | | |
| ATP Count per surface | | | | | Yes | | | | | | | |
| Optisolve 'Surface Score' | | | | | Yes | | | | | | | |
| Bioburden types (e.g. % gram-negative samples) | | | | | Yes | | | | | | | |
| Surface Contamination Data | | | | | | | | | | | | |
| Optisolve 'Surface Score' | | | | | Yes | | | | | | | |
| Occupancy Sensing Data | | | | | | | | | | | | |
| PPL per hr | | | | | | Yes | | | | | | |
| Rate in/out | | | | | | Yes | | | | | | |
| Historical Occupancy data | | | | | | Yes | | | | | | |
| Janitorial Sensing Data | | | | | | | | | | | | |
| Garbage Can % Full | | | | | | Yes | | | | | | |
| Water/Spill Sensor | | | | | | Yes | | | | | | |
| Handwashing Fill/Refill | | | | | | Yes | | | | | | |
| Predicted 'refill time' | | | | | | Yes | | | | | | |
| Tasklist and Execution Data | | | | | | | | | | | | |
| List of possible Tasks | | | | | | | Yes | | | | | |
| Ad hoc tasks | | | | | | | Yes | | | | | |
| Task Status and Completion Time | | | | | | | Yes | | | | | |
| Spill Alerts Data | | | | | | | | | | | | |
| Date, time, Location, Alert Type | | | | | | | Yes | | | | | |
| Room Cleaning Type (E.g. enteric of normal) Data | | | | | | | Yes | | | | | |
| Facilities Level Data | | | | | | | | Yes | | | | |
| Bed Monitoring Data | | | | | | | | | Yes | | | |
| Historical Culturing Data | | | | | | | | | Yes | | | |
| Historical Infection Data | | | | | | | | | | | | |
| Infection Type | | | | | | | | | Yes | Yes | | |
| Infection Location | | | | | | | | | Yes | Yes | | |
| Infection Date (Point in time OR start and end) | | | | | | | | | Yes | Yes | | |
| Current + Historical Weather Data | | | | | | | | | | | Yes | |
| Cleaning Policies (e.g. Surfacide every room vs only Cdiff) | | | | | | | | | | | | Yes |

Fig. 11

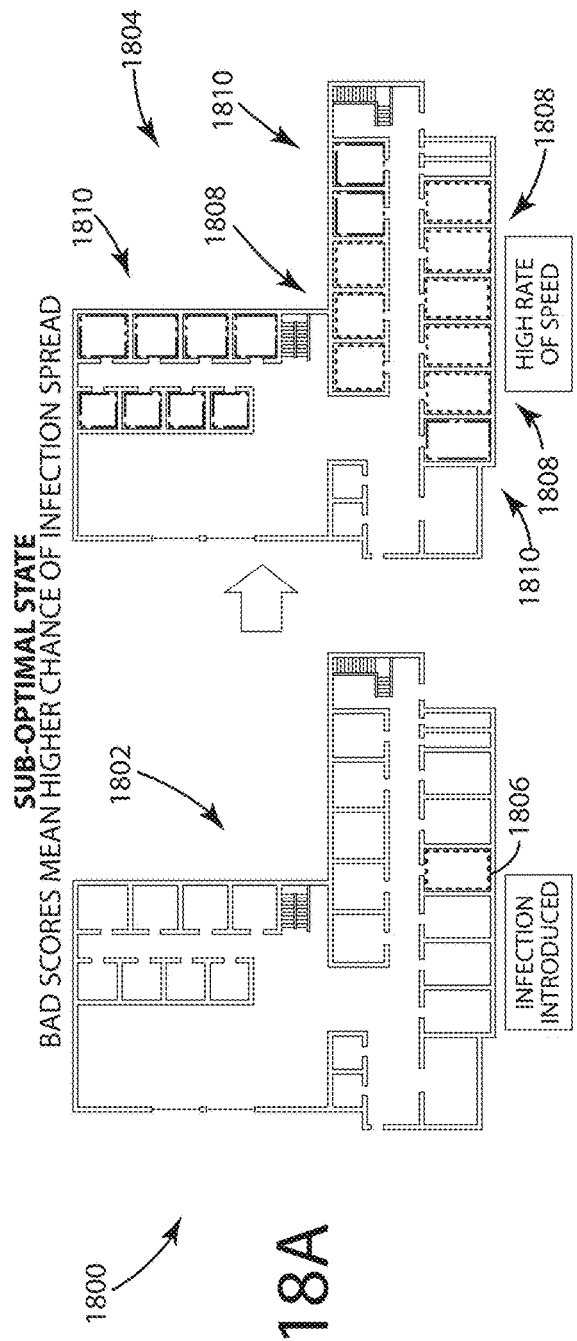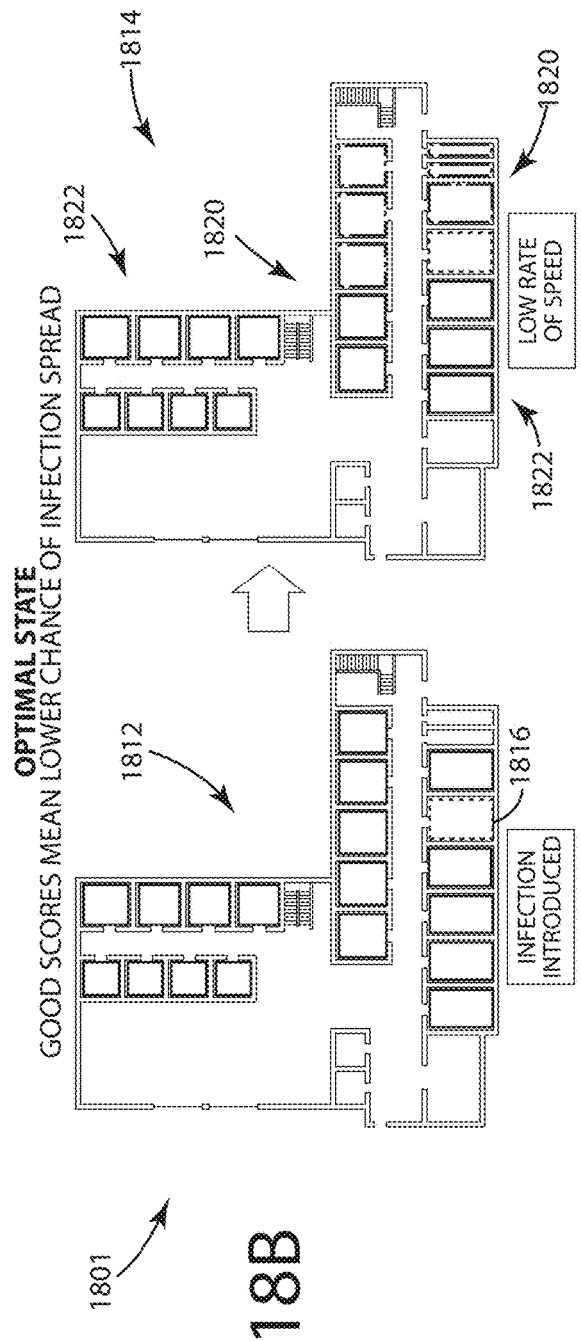
Fig. 18A
Fig. 18B

Overhead view of touch heat map

People counting & tracking

DISINFECTION TRACKING NETWORK

FIELD OF THE INVENTION

The present invention relates to tracking, and more particularly to systems and methods associated with tracking, predicting, and mitigating the spread of pathogens.

BACKGROUND OF THE INVENTION

A healthcare associated infection or hospital acquired infection ("HAI") is an infection that develops as a result of medical care. HAIs affect millions of people across the world and add billions of dollars to healthcare costs annually. It is well known that HAIs continue to present a significant health risk. A variety of efforts have been made to reduce the risks presented by HAIs. For example, there is increasing interest in performing germicidal activities in a hospital environment. This includes the growing use of UV disinfection systems to perform repeated disinfection of a wide range of objects. There are currently a number of different types of UV disinfection products available on the commercial market.

There has been dramatic growth in the use of networks to collect data relating to a range of activities in and around hospitals and other medical environments. Although some of these systems are already gathering data relating to personnel, asset tracking, electronic medical records, and patient health, the data is not being leveraged in a cost-efficient, reliable, and effective manner.

Other issues continue to persist with known systems such as lack of coordination from multiple workflows, understanding how to handle high touch areas and their infection impact, and the lack of robust engineered disinfection solutions. Some of these issues are exacerbated by healthcare environmental services cleaning and disinfection practices that are stretched thin.

Hospital cleaning and environmental sanitation is a core function of every hospital because it improves patient safety and is a necessary baseline for providing high quality of care. Conventional standard cleaning of an occupied patient room according to proper procedures can take 30 minutes or more, while terminal cleaning can take more than 45 minutes. However, often times there is pressure to complete these tasks in much less time with fewer resources, which can lead to poor outcomes. Furthermore, the amount of time to properly clean various hospital rooms can vary from hospital to hospital depending on a wide range of factors, such as traffic level and cleaning staff training.

It often can be difficult to understand, differentiate, and track inputs to a disinfection related pilot or study. Some attempts have been made to improve outbreak tracking efforts at a macro level, such as with computer models that often involve analysis of city-wide infection numbers in combination with airplane flights and travel data. However, the efficacy of these models is somewhat uncertain, and they do not appear to meaningfully leverage the vast amounts of infection related data available over emerging networked devices, let alone assist in mitigation efforts. Accordingly, there are ample opportunities for improving infection tracking and mitigation, especially within a local healthcare environment.

SUMMARY OF THE INVENTION

The present disclosure is generally directed to a system and method for tracking, monitoring, and collecting various data related to pathogens and the potential transfer of pathogens at a particular location or group of locations and potential travel pathways and travel opportunities. Various different data sets from a wide variety of different categories can be statistically analyzed and weighted to estimate pathogen level probabilities, transmission probabilities, and exposure probabilities. Some embodiments of the present disclosure relate to various ways to analyze policies, equipment, countermeasures, cleaning processes, infection data, biological surveillance and workflow and how they impact pathogen related outcomes. Some embodiments relate to systems and methods of tracking pathogen spread, predicting pathogen spread, reducing pathogen spread, or any combination thereof. Some embodiments relate to systems and methods using networked devices to track current or past pathogen spread or predict future pathogen spread based on data from various pathogen related sensors and location, movement, touch, or other physical sensors.

Combinations of different types of data can yield meaningful insights related to infection. The disclosure emphasizes physical data—such as data related to biological evidence, physical touch, and physical movement of equipment and people within an environment along a particular path or route. This data can manifest from combining data from different data sources, such as the following sensor based data sources which can be provided in real-time from multiple points within a facility; surface interaction data, handwashing compliance data, occupancy data, asset tracking data, and personnel tracking data, to name a few examples of the types of data that can be combined in pairs or in larger groupings. Further meaning can be extracted from these data sources when combined with additional extended-time based data sources, such as medical records, historical infection records, and biological surveillance data. Network connections to various devices enable collection of data from sources that previously were not readily available, let alone leveraged in combination in a robust and easily accessible manner, such as the case in some embodiments of the present disclosure that provide a disinfection portal. The data and combinations of data discussed herein and in connection with the disinfection portal can inform prediction analysis about potential disease outbreak, its probability of spreading, and its path traveling room to room throughout a location or throughout a group of locations. The data can also inform infection related trajectories and predicted impact analysis along with tailored countermeasures analysis based upon the severity of the trajectory.

One aspect of the present disclosure relates to a disease outbreak prediction analysis and countermeasure recommendation system and method. Some embodiments relate to identifying key contributions to disinfection performance with statistical analysis and a design of experiments. Effective infection countermeasures can be identified or verified with a statistical analysis of various sensor output and experimental design techniques. In other embodiments, systems and methods can include identifying and correcting a disinfection protocol deviation.

In some embodiments, an infection related score can be calculated based on various inputs and sensor output communicated over a network to a disinfection portal. The score can represent an estimated current score or a prediction of a future score on a particular infection related metric such as pathogen level, pathogen transmission level, pathogen exposure level, room cleanliness, opportunity for improved countermeasure, a cleaning opportunity, or essentially any combination thereof. An infection related score trajectory can also be determined or predicted based on various sensor output. Further, the system and method can include predicting changes to the infection related risk score trajectory. In some embodiments, an infection countermeasure recommendation can be provided based on a level of infection related risk, its trajectory, or both.

In general, one innovative aspect of the subject matter described in this specification can be embodied in a system and method for disinfection predictive analysis. The method can involve receiving, over a network at a disinfection predictive analysis portal, medical record entry data, asset location tracking data, employee tracking data, hand washing tracking data, cleaning data, disinfection equipment data, outbreak data, disinfection policy data, and biological surveillance data associated with a location. This data can be utilized by a processor of the disinfection predictive analysis portal to predict a probability of disease outbreak at the location. Specifically, the prediction can be made as a function of the medical record entry data, asset location tracking data, employee tracking data, hand washing tracking data, cleaning data, disinfection equipment data, outbreak data, disinfection policy data, and biological surveillance data associated with the location. Identifying, with the processor, a tailored countermeasure to mitigate the probability of disease outbreak to a predefined level as a function of severity of the probability of disease outbreak is another step of the method. Instructions can be communicated over the network to implement the tailored countermeasure at the location.

The foregoing and other embodiments can each optionally include one or more of the following features, alone or in combination. In particular, one embodiment includes all the following features in combination.

In some embodiments, the instructions to implement the tailored countermeasure include automatically increasing an amount of UV-C intensity output by each of a plurality of disinfection devices. The increase in the amount of UV-C intensity output by each disinfection device depends on the severity of the probability of disease outbreak.

In some embodiments, the instructions to implement the tailored countermeasure include automatically increasing an amount of UV-C disinfection cycle time of each of a plurality of disinfection devices, wherein the increase in the amount of UV-C disinfection cycle time of each of the plurality of disinfection devices depends on the severity of the probability of disease outbreak.

In some embodiments, the instructions to implement the tailored countermeasure include augmenting room cleaning associated with the location, wherein the augmenting depends on the severity of the probability of disease outbreak.

In some embodiments, the augmenting includes a combination of two or more of increasing dosage of a UV-C disinfection device, increasing frequency of cleaning the location, increasing length of time allotted for cleaning the location, verifying compliance with cleaning procedures with sensor data, and marking high touch surfaces for monitoring the quality of cleaning and disinfection.

In some embodiments, the augmenting room cleaning includes augmenting a cleaning protocol by at least one of using higher dwell time disinfectant, increasing frequency of cleaning high touch surfaces, and verifying cleaning of high touch surfaces.

In general, one innovative aspect of the subject matter described in this specification can be embodied in a networked system for disinfection predictive analysis of a hospital having a plurality of hospital rooms. The networked system includes a disinfection application programming interface (API) associated with a disinfection predictive analysis portal. The disinfection API is configured to collect tracking data by interfacing, over a network, a tracking data source, collect biological surveillance data by interfacing, over a network, a biological surveillance data source, collect historical infection data by interfacing, over a network, a historical infection data source, collect facility data by interfacing, over a network, a facility data source, collect surface data by interfacing, over a network, a surface data source, and collect cleaning data by interfacing, over a network, a cleaning data source. The networked system includes a processor associated with the disinfection predictive analysis portal and is configured to predict a probability of disease outbreak at each of the plurality of hospital rooms based on the tracking data, biological surveillance data, historical infection data, facility data, surface data, and cleaning data. It should be understood that the processor can include one or multiple processors and that the processor(s) can be local, remote, distributed (e.g., cloud based processing resources), or a combination thereof. The processor is configured to identify a combination of a plurality of tailored countermeasures to mitigate the probability of disease outbreak in each of the plurality of hospital rooms to a predefined level as a function of severity of the probability of disease outbreak for that hospital room. The processor is configured to communicate, over the network, instructions to a plurality of devices associated with the plurality of hospital rooms to implement the combination of the plurality of tailored countermeasures to mitigate the probability of disease outbreak in each of the plurality of hospital rooms to the predefined level as the function of severity of the probability of disease outbreak for that hospital room.

The foregoing and other embodiments can each optionally include one or more of the following features, alone or in combination. In particular, one embodiment includes all the following features in combination.

In some embodiments, the cleaning data includes disinfection equipment data and hand washing data. The historical data can include historical disease outbreak data. The facility data can include disinfection policy data, hospital room layout information, and in-room air treatment data. The tracking data includes asset location tracking data and employee location tracking data.

In some embodiments, the instructions to implement the combination of tailored countermeasures include automatically increasing an amount of UV-C intensity output by each of a plurality of disinfection devices. The increase in the amount of UV-C intensity output by each of the plurality of disinfection devices depends on the severity of the probability of disease outbreak.

In some embodiments, the instructions to implement the combination of tailored countermeasures includes automatically increasing an amount of UV-C disinfection dosage of each of a plurality of disinfection devices. The increase in the amount of UV-C disinfection dosage of each of the plurality of disinfection devices depends on the severity of the probability of disease outbreak.

In some embodiments, the instructions to implement the combination of tailored countermeasures includes augmenting room cleaning associated with the plurality of hospital rooms. The augmenting depends on the severity of the probability of disease outbreak of the respective hospital rooms.

In some embodiments, the augmenting includes a combination of two or more of: (a) increasing dosage of a UV-C disinfection device; (b) increasing frequency or intensity of cleaning the location; (c) increasing the length of time allotted for cleaning the location; (d) verifying compliance with cleaning procedures with sensor data; (e) marking high touch surfaces for monitoring quality of cleaning; (f) electronically tracking cleaning policies, for example including tracking compliance and non-compliance with cleaning policies; and (g) disinfection processes.

In some embodiments, the augmenting room cleaning includes augmenting a cleaning protocol by at least one of using higher dwell time disinfectant, implementing terminal cleaning equipment, increasing frequency of cleaning high touch surfaces, and verifying cleaning of high touch surfaces.

Another innovative aspect of the subject matter described in this specification can be embodied in a method for tracking disinfection performance within a hospital having a plurality of rooms. The method includes using a networked system to track; (a) data related to the pathogen level in each of the plurality of rooms of the hospital; (b) data related to pathogen transmission from each room of the hospital to other rooms of the hospital; and (c) data related to pathogen exposure to humans in each of the plurality of rooms of the hospital. The method can include statistically analyzing the data and estimating statistical probabilities for the pathogen level in each of the plurality of rooms of the hospital, pathogen transmission from each room of the hospital to other rooms of the hospital, and pathogen exposure to humans in each of the plurality of rooms of the hospital. The method can also include designing experiments to determine key contributing factors to the statistical probabilities and determining an overall infection related score for each of the hospital rooms indicative of probability of pathogen level, probability of pathogen transmission, and probability of pathogen exposure to humans in each respective hospital room. The method can include running the experiments, tracking pathogen level outcomes based on sensor data received over the network, pathogen transmission outcomes based on sensor data received over the network, and pathogen exposure outcomes based on sensor data received over the network. Verifying efficacy of the overall infection related score for each of the plurality of rooms of the hospital based on the pathogen level outcomes, pathogen transmission outcomes, and pathogen exposure outcomes can also be included in the method.

The foregoing and other embodiments can each optionally include one or more of the following features, alone or in combination. In particular, one embodiment includes all the following features in combination.

In some embodiments, the method includes determining, by statistical design of experiments, a healthcare protocol deviation.

In some embodiments, the method determines an infection related score trajectory and adjusts the infection related score trajectory based on the identified healthcare protocol deviation and potential mitigation.

In some embodiments, the method includes instructing a plurality of devices within the hospital to adjust operation to alter the infection related score trajectory to a predefined infection related score within a predefined timeframe. The size of adjustment to operation of the plurality of devices within the hospital depends on the severity of the infection related score trajectory.

One innovative aspect of the subject matter described in this specification can be embodied in a system for tracking disinfection performance as a design of experiments. The system includes a disinfection portal including a database and processor and is connected to a network. The disinfection devices communicate with the disinfection portal over the network, and are configured to disinfect target disinfection areas and communicate pathogen impact data. The system also includes movement tracking devices configured to track movement of a plurality of assets, touch tracking sensors configured to track physical touches and communicate infection exposure impact data to the disinfection portal over the network.

The processor is configured to statistically analyze the pathogen impact data, infection transmission impact data, and infection exposure impact data. It is also configured to estimate, based on the statistical analysis, measured pathogens and measured reduction performance, measured pathogen transfer, statistical probabilities for pathogen level, infection transmission, and infection exposure. The processor is configured to execute a design of experiments to determine a plurality of key contributing factors to the statistical probabilities for pathogen level, infection transmission, and infection exposure and to determine an overall infection related score indicative of probability of pathogen level, probability of infection transmission, and probability of infection exposure. It is also configured to track pathogen level outcomes based on pathogen impact data received over the network, pathogen transmission outcomes based on infection transmission impact data received over the network, and pathogen exposure outcomes based on infection exposure impact data received over the network, and to verify efficacy of the overall infection related score based on the pathogen level outcomes, infection transmission outcomes, and infection exposure outcomes.

Another innovative aspect of the subject matter described in this specification can be embodied in a disinfection tracking system for a hospital having a plurality of hospital rooms. The disinfection tracking system includes a design of experiments (DOE) engine, and has occupancy sensors associated with the hospital rooms located throughout the hospital. The sensors sense occupancy data in the hospital rooms and communicate the occupancy data to the DOE engine over a network, which can include data indicative of location. For example, video or radar based occupancy detection can detect touches and body movement to better understand the human touch pathway within the room informing cleaning and transmission pathways. The disinfection tracking system can also include hand washing sensors associated with respective hand washing stations located throughout the hospital. Sensed handwashing data is communicated to the DOE engine over the network and can include data indicative of location. Mobile and stationary equipment sensors can be associated with their respective mobile and stationary equipment. The mobile equipment sensors primarily focus on sensing hospital room location data while the stationary equipment sensors primarily focus on sensing human activity data, both of which can be sent to the DOE engine over the network. The DOE engine is configured to determine an infection related score based on sensor data relative to an acceptable measured pathogen level based on sensor data during a calibration period.

The foregoing and other embodiments can each optionally include one or more of the following features, alone or in combination. In particular, one embodiment includes all the following features in combination.

In some embodiments, the infection related score is indicative of an estimated current score of at least one of: pathogen level; pathogen transmission level; pathogen exposure level; a combination of pathogen level, transmission level, and exposure level; room cleanliness opportunity for improved countermeasure; and a cleaning opportunity of at least one of a person, room, building, facility, complex, hospital, or hospital network. In other embodiments, the infection related score is indicative of a prediction of a future score.

In some embodiments, the plurality of mobile equipment sensors sense data indicative of at least one of exacerbating or mitigating pathogen transmission, pathogen exposure, pathogen transmission, or pathogen exposure.

In some embodiments, the stationary equipment includes air treatment systems; as well as heating ventilation and cooling (HVAC) systems. In some embodiments, the mobile equipment includes asset tracking equipment.

In some embodiments, a starting data set for the DOE engine includes biological evidence, infection transfer probabilities, physical touch tracking data, physical and asset tracking data, and infection mitigation data.

Another innovative aspect of the subject matter described in this specification can be embodied in a mobile application for tracking user health, transmission, and exposure. The mobile application can include an interface for self-reporting symptoms that can aid in early infection detection. The mobile application can be configured to record user travel path data, such as location data and time data. The user travel path data can be utilized to discover whether a user may have a heightened exposure risk due to their travel path crossing paths with another user using the mobile application with a positive diagnosis. That is, the mobile applications of the various users can communicate to each other or to a shared system in the cloud that can analyze the user path data in connection with infection diagnosis data to assess whether users were exposed due to co-locating with other users reporting or confirmed to have an infectious disease. The mobile application can also utilize the data from user paths of known infected users in order to display graphical and textual information related to probabilities of exposure at particular locations, paths infected users, and transmission probabilities related to attending certain locations. The mobile application can also include alarm capabilities to indicate an infected user is approaching, is in the vicinity, or that a particular area's infection score is trending upward. Further, the mobile application can also collect transmission data about the infected user that can weigh the transmission probabilities. For example, bathroom visits, hand washes by recognizing the sound of a faucet, and reflecting the amount of time spent at that location. The application can provide appropriate mitigation strategies to both infected and non-infected users. For infected users, the mobile application can recommend pathing away from non-infected users and for infected users, vice versa.

Another innovative aspect of the subject matter described in this specification can be embodied in a user interface showing infection related scores. A disinfection portal can collect data from a variety of data sources that can be used to calculate an infection related score, such as pathogen spread probability, pathogen transmission probability, pathogen exposure probability, or other probabilities related to infectious diseases. The score can be related to sensor data for a particular location and can be sub-divided into sub-locations that are based on sensor data for those sub-locations. For example, a hospital may have many rooms, such as patient rooms, hallways, lobbies, waiting areas, lab areas, operating rooms, bathrooms, cafeterias, etc. Each of these rooms may include various different types of sensors. The sensors can include physical sensors that can sense a physical characteristic, such as touch, movement, presence, occupancy, location, position, and other human physical activity. The sensors can also include infection related sensors that can sense an infection related characteristic. The infection characteristic can be positive or negative, that is, it can be a characteristic that is indicative of pathogen level, pathogen transmission, pathogen exposure, or a change positive or negative of any of them. Further, the infection characteristic can include direct or indirect sensor data, that is, data which is directly linked or indirectly linked pathogen level, pathogen spread, or pathogen exposure. Some examples include how often a person touches their face, how often a person uses the bathroom, how often a hospital room is cleaned, hospital cleaning policy, air treatment configuration, terminal cleaning procedure, biological waste handling, and cleaning verification procedures, to name a few.

The various aspects and embodiments of the disinfection portal, disinfection performance tracking, disease outbreak prediction, and infection score calculation provide robust and efficient systems and methods for approaching tracking infection transmission throughout an environment and countermeasure impact. The various aspects and embodiments provide a framework for not only learning and understanding how infection spreads within a hospital environment, but also provides a systematic way for identifying key contributors to disinfection performance with statistical analysis and a design of experiments. These various insights can be packaged and presented in a helpful graphical user interface on a disinfection portal. An infection related score that reflects pathogen level, pathogen transmission probability, pathogen exposure, or some combination thereof can be mapped at a room level based on objective, physical, and data sensed from various devices located throughout the hospital that automatically communicate to the portal over a network enabling real-time updating of the disinfection status of not only the hospital at large, but specific room by room disinfection status. Should an outbreak occur or a significant increase in infection score, the portal can provide real-time updates that graphically show not only where the issue is occurring, but also predicting and showing where the infection is most likely to spread and in what timeframe or trajectory. The disinfection portal can automatically initiate or recommend infection mitigation instructions in response to a threshold infection score or predicted infection score. Such mitigation can be experimentally verified to provide a specifically tailored reduction in the trajectory of the infection score based on the severity of the score or trajectory of the score.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components. Any reference to claim elements as "at least one of X, Y and Z" is meant to include any one of X, Y or Z individually, and any combination of X, Y and Z, for example, X, Y, Z; X, Y; X, Z; and Y, Z.

BRIEF DESCRIPTION OF THE DRAWINGS

FIG. 10 shows one embodiment of a disinfection network matrix.

FIG. 11 shows another embodiment of a disinfection network matrix.

FIGS. 18A-B show optimal and sub-optimal states for a wing of a hospital.

DESCRIPTION OF THE CURRENT EMBODIMENTS

Figure 1:
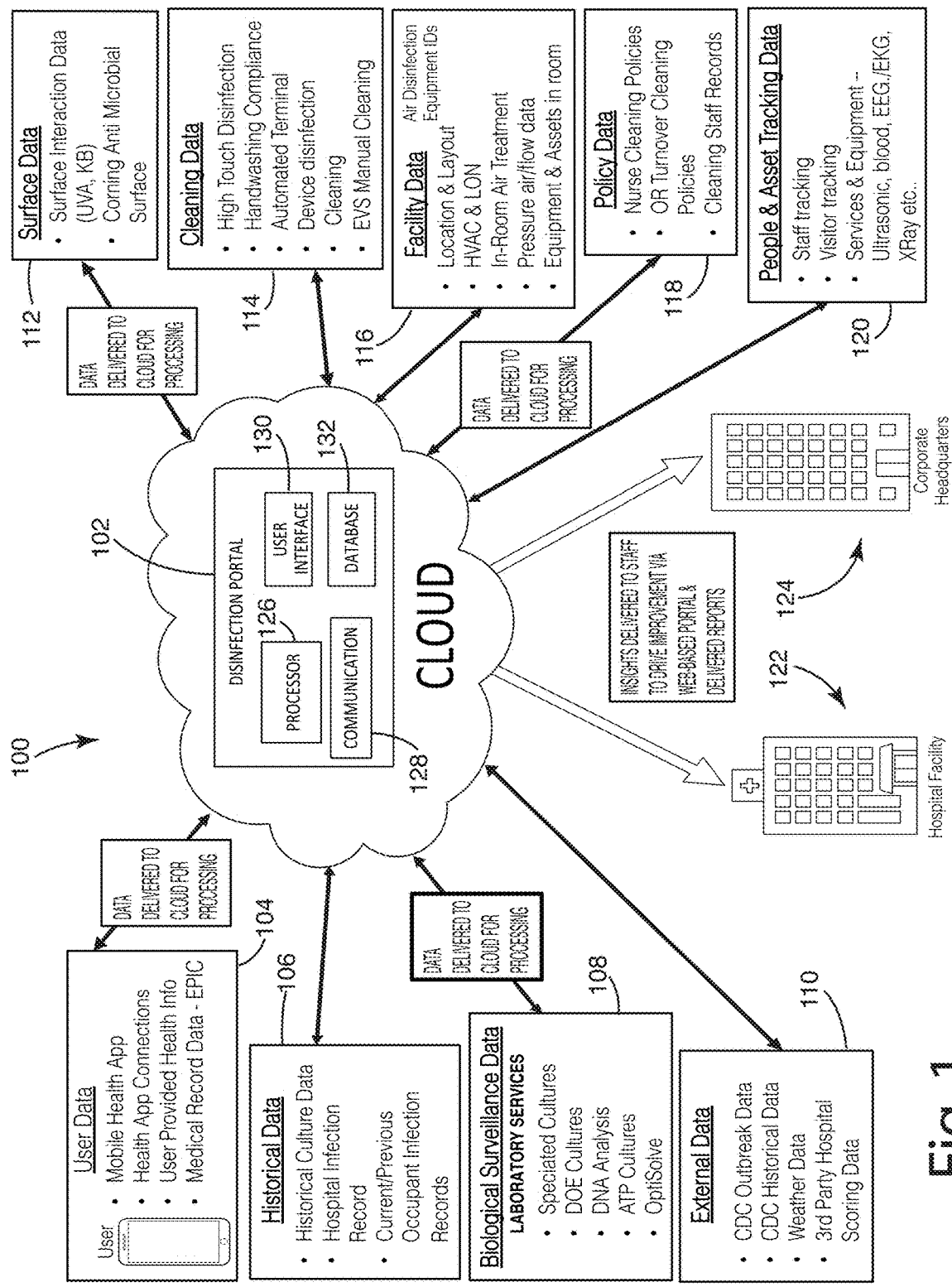
FIG. 1 illustrates a representative block diagram of one embodiment of a disinfection portal system.

One exemplary embodiment of a disinfection tracking network system 100 is illustrated in FIG. 1. The depicted embodiment includes a variety of different data sources 104-120 that are connected to a disinfection portal 102 through a network, such as the Internet. The disinfection portal 102 includes computer hardware that can process the data received from the various data sources 104-120 and output meaningful insights that drive improvement, for example via web-based dashboard available through network connection to the portal, reports, and automated or semi-automated device instructions that change disinfection policy related to disinfection devices, disinfection workers, disinfection procedures, disinfection products, or any other aspect relating to curtailing, mitigating, preventing, reducing, learning about, infection, disease outbreak, pathogen levels, transmission probabilities, or exposure probabilities.

Throughout this disclosure reference may be made to specific infectious agents or resulting conditions, such as bacteria, viruses, fungi, protozoans, helminths, pathogens, germs, diseases, infections, microbial contamination, or other similar terms. Reference may also be made to an infection, sickness, disease, illness, or other similar terms. Further, there may be references to infection related scores, pathogen, infection, disease, illness transmission or exposure or probabilities thereof, or a change or trajectory of these various metrics. Along the same lines, there may be reference to cleaning, disinfecting, decontaminating, purifying, and sterilizing. These various descriptors may be utilized throughout the disclosure in connection with certain embodiments of systems, devices, and parameters, for example disinfection portal, disinfection tracking system, disinfection score, infection trajectory, pathogen level, pathogen transmission probability, and infection prediction system, to name a few. It is to be understood that the phraseology and terminology used herein are for the purpose of description and should not be regarded as limiting.

Returning to FIG. 1, one embodiment of a disinfection tracking network together with examples of key starting input and output elements is illustrated in a representative fashion. The system is configured to tracking physical and biological data in conjunction with historical and policy data to gain a new perspective. The disinfection portal 102 can include a processor 126, user interface 130, communication module 128, and database 132, among other components. In operation, the disinfection portal 102 can receive or access data from the various different data sources 104-120. The data can be processed by the processor 126, as will be described in more detail herein, and can output meaningful insights or instructions. The disinfection portal 102 can be utilized in connection with a variety of different locations of varying sizes. For example, the disinfection portal can be utilized in connection with a single residential home, storefront, apartment, or condominium complex. However, the disinfection portal is particularly suited, as depicted in FIG. 1, for use in connection with a hospital facility 122 that may have an office or corporate headquarters 124 integral or at a remote location. The hospital facility can have a plurality of different rooms and areas which can be monitored by various sensors to track physical activity and movement throughout the hospital, as will be discussed in more detail later. In addition, various data related to calculating an infection related score for the hospital, or a sub-portion of the hospital, such as a hospital room or hallway, can be collected. This can include the physical tracking sensors as well as many other types of sensors. One embodiment of a disinfection portal 102 collects data from a user data source 104, a historical data source 106, a biological surveillance data source 108, external data sources 110, surface data sources 112, cleaning data sources 114, facility data sources 116, policy data sources 118, and people and asset tracking data sources 120, which will now be discussed in more detail.

User data sources 104 refer to data particular to a user or group of users, for example, mobile health applications where users self-report symptoms and feelings or mood information. The user data can include medical record data, such as from the Epic medical record system, which is one of the electronic medical record systems used by a large number of health care organizations in the United States. The user data available from user data sources 104 can also include user provided health information, such as information provided during a hospital intake procedure. Further, the user data may relate to health care application connections. All of the user data can be uploaded to the disinfection portal 102 for analysis.

Infection related historical data sources 106 refers, generally, to data collected about past events and circumstances pertaining to infection. Historical data can include data generated manually or automatically. Examples of historical data can include historical culture data, hospital infection records, and current or previous occupant infection records.

Biological surveillance data 108 refers to data from laboratory services that perform analysis of cultures or other biological samples. For example speciated cultures, design of experiments cultures, Deoxyribonucleic acid ("DNA") analysis, Adenosine Triphosphate ("ATP") cultures, and microbial imaging are all examples of biological surveillance data.

External data sources 110 can include various other data sources. These data sources typically refer to data that is external to not only the location where the disinfection tracking network, disinfection portal, and its sensors are located, but typically that is external to the organization from which data is being collected by the disinfection portal. Examples include CDC outbreak data, CDC historical data, weather data, third party hospital infection scoring data, or other third party sources.

Surface or touch data sources 112 can include data that informs the disinfection portal about the pathogen level of the various surfaces throughout the hospital facility 122 or other locations being monitored. The surface data can stem from devices, such as keyboards or disinfection devices. For example, some embodiments of a disinfection device include various sensors that can collect different types of data that include patterns indicative of surface data—for example, the use of accelerometers to detect user surface touches. Or a combination of passive infrared sensor data and accelerometer data to detect certain types of touches, like wiping of a keyboard or monitor with a disinfectant wipe. More specifically, various surface data collection techniques and disclosure is included in U.S. Provisional application No. 62/985,976, filed on Mar. 6, 2020 to Baarman et al., entitled "UV DISINFECTION PLATFORM", which is herein incorporated by reference in its entirety. In addition to surface data that is actively collected by way of sensor, surface data can also include data about the particular surfaces installed and their characteristics. For example, some surfaces are particularly susceptible to microbial collection, while others are more resilient. The makeup of the hospital surfaces can influence the design of experiments and any resulting models used in connection with the disinfection portal prediction analysis or scoring system. In some embodiments, the surface data may include data about how many and the location of anti-microbial surfaces, such as surfaces composed of Antimicrobial Gorilla® Glass, available from Corning®, or surfaces coated with an anti-microbial coating.

Cleaning data sources 114 can come from a variety of different places. The cleaning data can include high touch disinfection data. It can also include environmental services manual cleaning (EVS) data, such as cleaning times, checklists about what particular cleaning tasks were performed, verification testing results, and similar types of data. The cleaning data can also include cleaning device disinfection data from various equipment used in the disinfection process, such as UV disinfection devices, automated terminal cleaning devices or robots, and handwashing compliance data from handwashing sensor data.

Facility data 116 can include location and layout data, which in this embodiment plays a role in mapping the other data sources to particular locations or sub-locations allowing for an increased understanding of the other data. Other examples of facility data can include data collected from the heating, ventilation, and air conditioning (HVAC) unit. The facility data can include almost any data from a device or fixture that resides within the facility. Especially devices that have network capability, either wirelessly through a hospital Wi-Fi, mesh, or other type of network. Some hospitals include a local operating network ("LON"), which is a networking platform specifically created to address the needs of control applications. The platform is built for communication over twisted pair, power lines, fiber optics, and RF. It is generally used for automation of various functions within buildings, such as lighting and HVAC. Other examples of facility data can include air treatment, air flow, and air pressure data. Another large sub-category of facility data is the equipment identifiers ("ID") of various equipment and assets in the rooms. An identifier for a stationary device installed at a particular location can also be utilized as a look-up to determine the device's location.

Policy data 118 can refer to different policies that are associated generally with cleaning and disinfection procedures. It can also include data about procedures and responses if a disease outbreak occurs. Some more specific examples of policy data can include nurse cleaning policies, operating room turnover cleaning policies, cleaning staff records, and regular and terminal cleaning checklists. Further, policy data can include essentially any information published by the association for professionals in infection control and epidemiology ("APIC") or other organizations that drive healthcare/infection/outbreak policy and procedures. For example, APIC publishes prevention and control techniques as well as education programs for healthcare personnel, which help shape and form policy specifically related to limiting the cause and spread of hospital-acquired infections.

People and asset tracking data 120 can include data about the movement of people and assets throughout the hospital, including their entrance and exit. Tracking data can be helpful in building and informing infection path assessments and predictions. Staff and visitors may wear badges or other sensors that can be utilized with other equipment throughout the hospital to track movement on a user level. Alternatively, or in addition, throughout the facility different cameras, imaging sensors, and line of sight sensors may be installed that inform human movement throughout the hospital. In addition, lower resolution data can also provide meaningful data, such as door sensors that track how many times a door was opened over a period of time, and estimating traffic through that particular door. In aggregate this type of data can depict traffic flow throughout the hospital, which can be useful when more granular data is not available or resource prohibitive for other reasons. Tracking physical assets, such as medical carts and other equipment, can also be useful, as a corollary of human movement, but also because the movement of equipment can also contribute to pathogen spread throughout the hospital.

For all of these different data sources 104-120, the data can be provided over a network to the disinfection portal. The disinfection portal can process the data locally using its processor, for example using a variety of data science, machine learning, and data analytic libraries. For example, Pandas is a Python software library for data manipulation and analysis that offers data structures and operations for manipulating numerical tables and time series. Alternatively, or in addition, the data can be directly or indirectly provided to a cloud service for storage and/or processing, such as Amazon Web Services ("AWS"). Cloud processing services can provide access to processors for computation and storage. They also can provide access to machine learning and artificial intelligence infrastructure. Further, cloud processing services can provide access to data warehouses, data lakes, analytics, and Internet of Things. Generally, a data lake is a centralized repository that allows storage of structured and unstructured data at any scale. Data lakes can be particularly suited for predicative analysis, such as predicting infection related scores.

It is worth noting that various data sources can also be internal to the hospital or the hospital network. That is, data can be polled or pulled from the hospital itself in many cases. For example, many of the data sources are not third party and need not be routed through the cloud if the processing is being performed by a local processor. For example, cleaning, surface, user, facility, policy, and tracking data can all be local data sources. Further, these various data sources may not be singular data sources but rather certain categories of information may be collected from multiple different data sources that provide different subcategories of information or redundant information which can be utilized for verification or speed purposes. The various data available from the local hospital network can be categorized as such and may include policies, construction data (such as whether the hospital used disinfecting paint), anti-microbial surfaces, or other construction metrics that can affect infection spread calculations. In some cases, the system can be configured to calculate one or more different infection related scores based on information, but for a variety of reasons may not store the underlying data used in the calculation or may not store the data longer than a predetermined amount of time. For example, data for EMR can essentially pass through the system without being stored. Further, the data can be used to store and track HAI related data.

In some embodiments, a disinfection application programming interface (API) can be provided that is associated with the disinfection portal. In the current embodiment, the disinfection API is configured to collect data from all of the different data sources 104-120. It can also be configured to provide a wide range of outputs, for example infection related scores for particular rooms, hospitals, or groups of hospitals.

Thus far the disinfection portal 102 and the disinfection tracking network 100 generally have been described in connection with a single hospital 122. It should be understood that the disinfection portal can be scalable, such that it can provide disinfection predictions, assessments, and recommendations with respect to individual rooms, wings, buildings, or the entire hospital. Further, it can scale upwards to include data collection and analytics with respect to a group of hospitals from a single organization. Insights may be learned by comparing and contrasting various infection mitigation opportunities across hospitals.

Ultimately, the disinfection tracking network and disinfection portal 102 can provide a graphical user interface to provide users with information about the current infection related insights made by the system, as well as predictions and recommendations. Further, as discussed in more detail later, the system can automatically implement recommendations to mitigate infection spread, such as controlling dosage of UV disinfection devices or changing polices, such as cleaning frequencies. Through a design of experiments, these and other tailored countermeasures can be provided to stop and contain the spread of pathogens throughout a hospital. Tailoring, in this context, refers to configuring the particular countermeasure or set of countermeasures based on the severity of the pathogen level or outbreak. As an example, the UV disinfection dosage can be increased proportionally according to a predefined model based on the trajectory of pathogen spread score—that is, rooms with a higher score can have characteristics of the disinfection device automatically updated dependent on how high the pathogen spread score or other infection related score is in that particular room. Further, not only the raw score can be accounted for, but the trajectory of that score—where the score has a large trajectory, the characteristics can be set in proportion to lower the trajectory faster, whereas if the trajectory were lower, the characteristics can be set such that the trajectory does not decrease as fast. This can be a meaningful methodology because there is a balance to be struck by the number and intensity of the various countermeasures and the infection level or infection spread rate.

The graphical user interface can present information regarding the prediction of pathogen spread risk to the user. The pathogen spread risk can be calculated using a processor 126, or distributed processing such as available by a cloud service and can be based on the various data sources discussed herein. The infection tracking network and associated components can also reduce the pathogen spread by recommending and taking mitigating or remedial actions based on the pathogen spread risk score. In some embodiments, the data sources are connected via networked devices and pathogen spread throughout the hospital and can be tracked according to multiple pathogen factor sensors, each sensing either mitigating or exacerbating factors, and multiple movement related sensors. Together the pathogen factor sensors and movement sensors enable source discovery, for example data patterns that have an increased statistical probability of pathogen transmission or exposure might include occupancy sensor data combined with hand washing data showing that at a particular range of time there was a statistically significant infection event. From there, the various data can be utilized to track the statistically likely infection spread path. For certain contagions it may be possible to track its transmission among a particular route and prevent further transmission (by identifying and communicating with the infected person or cleaning the contagion laden asset) and exposure (by limiting contact and proximity to the infected person or asset).

In some embodiments, this process method and system is designed to create a laboratory system and methods for learning and understanding environments and how they perform. In essence, the present disclosure provides methods to create a laboratory approach to tracking environmental and disinfection impact. These methods of tracking disinfection efforts and related methods can include interactions and asset tracking, staff and visitor tracking, handwashing compliance and behavior, biological surveillance, infections, infection history, policies, room activity, and applied countermeasures.

The various embodiments can include use of a network and method and system for disinfection predictive analysis. The use of multiple inputs such as medical record entry touches, asset tracking for equipment travel, employee tracking, hand washing tracking, cleaning record and workflow, equipment and countermeasures applied, ongoing and past outbreak data, policies in place, and biological surveillance data to predict areas of higher potential for outbreaks and opportunities for improved countermeasures and cleaning.

Further, the method and network for tracking performance as a design of experiments is also provided. This can involve using a networked system to track aspects and inputs that may impact disinfection, transmission, and exposure. Statistically these inputs can be analyzed to arrive at statistical probabilities. From there, calculations of the overall probabilities of key contributors using design of experiments calculations for statistical outcomes can be performed. The available information from the various data sources can enable experimentation, learning, and proving efficacy through formal experimentation and tracking outcomes in the network. A statistical model can be built into the disinfection portal that provides simple and effective real-time reporting regarding a variety of infection related insights.

Health and safety protocols often are used to drive performance. It can be difficult to understand deviations from policies and protocols and changes in trajectories let alone the underlying impact of the trajectories. By having a system that can network with the various data sources, utilizing data streams as inputs to define protocol and policy changes or deviations can be recognized. That is, desired state alignment, such as discussed in connection with FIG. 19, can be used for predictions and also corrective actions and reporting. The resultant trajectory provided can allow for a correction to an optimal state.

Figure 19:
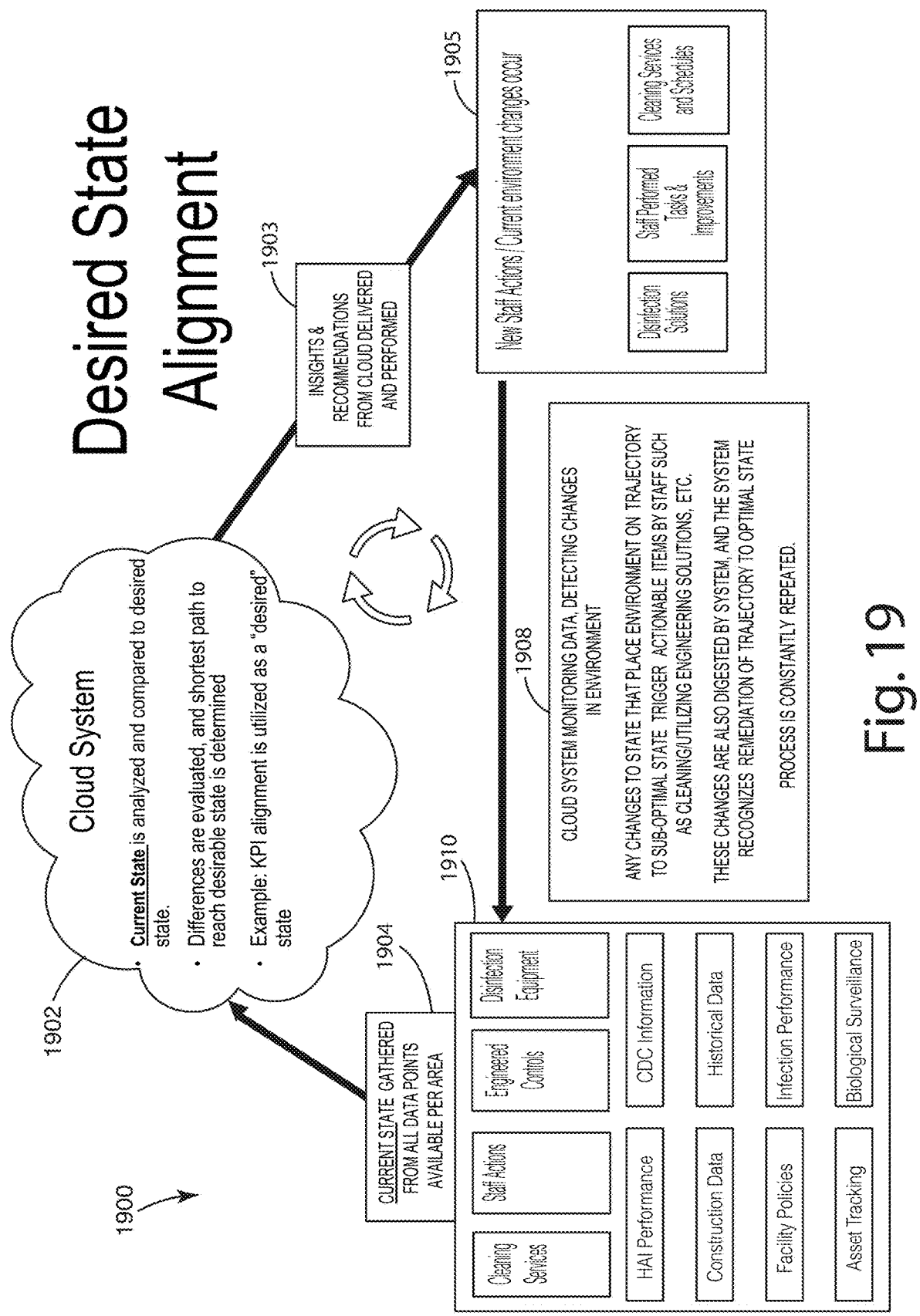
FIG. 19 shows a representative flow diagram of desired state alignment.

FIG. 19 shows a desired state of alignment driving specific staff actions based on actual physical and biological expectations 1900. The cloud system 1902, such as the disinfection tracking network depicted in FIG. 1, can be configured to gather current state information 1904 from available data sources 1910 that may be generally available or available per location or area. Then, the cloud system 1902 can analyze the current state and conduct a comparison to a desired state (e.g., infection level or pathogen spread risk score). Differences between the two states can be evaluated and a shortest path to reach a desirable state can be determined by the system. For example, key performance indicator alignment can be utilized as a "desired" state.

Insights and recommendations 1903 from the cloud system can be delivered and executed, for example by staff carrying out new actions (such as new cleaning tasks, and improvements to existing cleaning tasks), changes to disinfection device parameters or installation of disinfection devices, and changes to cleaning services and schedules 1905.

As the various countermeasures are enacted the current environment will see changes occur, all the while the cloud system can continue to constantly monitor data, detecting changes in the environment. Any changes to state that place the environment (e.g., hospital, wing of hospital, or hospital room) on a trajectory to sub-optimal state will trigger actionable items by staff such as cleaning/utilizing engineering solutions 1908. These changes are also reflected in the data sources 1910 and the current state information 1904 digested by the system, and the system 1902 recognizes remediation of trajectory to optimal state. The process can be constantly repeated whenever the state is altered. An example of this is perhaps best shown in the representation of FIGS. 18A-B, which illustrate the difference between infection spread in an optimal state vs. a sub-optimal state. In sub-optimal state 1800, when infection is introduced 1802 at a particular location such as a room 1806, the sub-optimal state 1804 leads to a high rate of spread of infection. For example, rooms close to where the infection outbreak occurred 1808 have a high chance of receiving the pathogens by way of transmission due to the sub-optimal state. The rooms farther away 1810 have a lower chance. Contrast this with the optimal state 1801 where when the infection is introduced 1812 to the room 1816, the spreading 1814 is contained to moderate chance of transmission in some nearby rooms 1820 while other rooms 1822 have virtually no impact. This can be due to a variety of reasons, such as procedures to quarantine a patient, adequate repeated cleanings, where the rooms with slight increase 1820 are at the tail end of a cleaning cycle, or a variety of other countermeasures that are in place to keep the optimal state.

Figure 20:
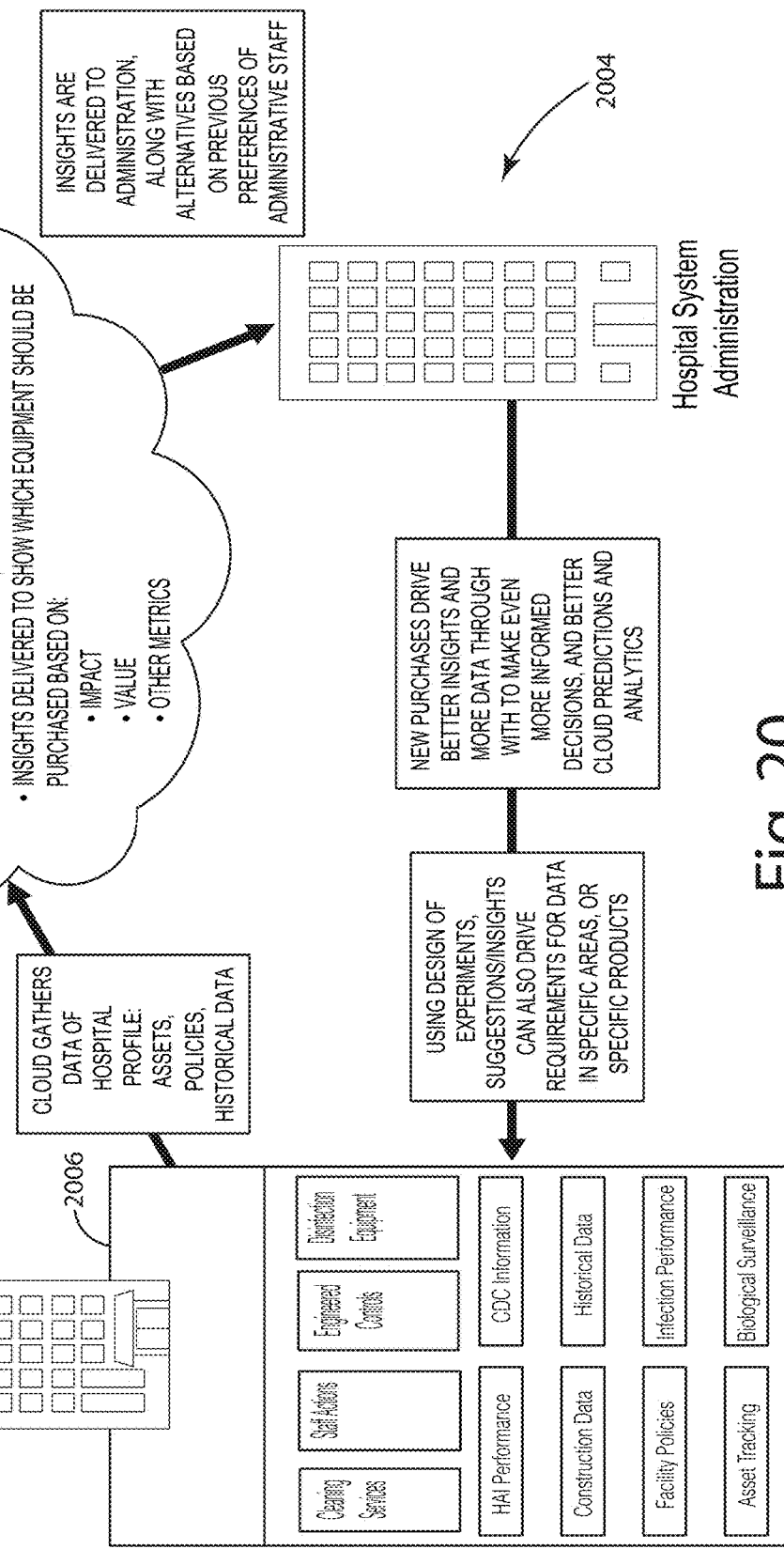
FIG. 20 shows a representative flow diagram of a disinfection network system.

A flowchart 2000 showing one exemplary system flow is depicted in FIG. 20. System 2002 can be configured to provide best positive options to optimize resources for the biggest impact. As before, data regarding the current state can be collected 2006, such as a hospital disinfection profile. Then, the cloud system 2002 can process data, weighing and comparing effects of equipment and historical data. Weighted scores can be compared to other systems and best-in-practice profiles, along with data on cost and time-to-implementation, and a statistical solution can be arrived at for a best solution or several options for solutions. Insights can be delivered to administration 2004, such as recommendations for equipment purchases based on impact, value, or other metrics. Put simply, the disinfection tracking network can assist in optimizing resources spent on disinfection equipment and policy. Building an environment as a formal design of experiments with performance driven outcomes can essentially make the environment a laboratory. The statistically proven outcomes enable weightings to be given to items that have a statistically larger impact on the environment. The ongoing study of the environment, along with biological surveillance, creates a laboratory for enabling the probabilities for impact and long terms cost analysis. The cost impacts can be calculated by understanding present fees and fines paid and the potential impact to these costs based on these statistical outcomes in a known environment. For other environments, biological surveillance combined with the statistical impact can be used as a health rating and impact by countermeasure respectively.

Figure 17:
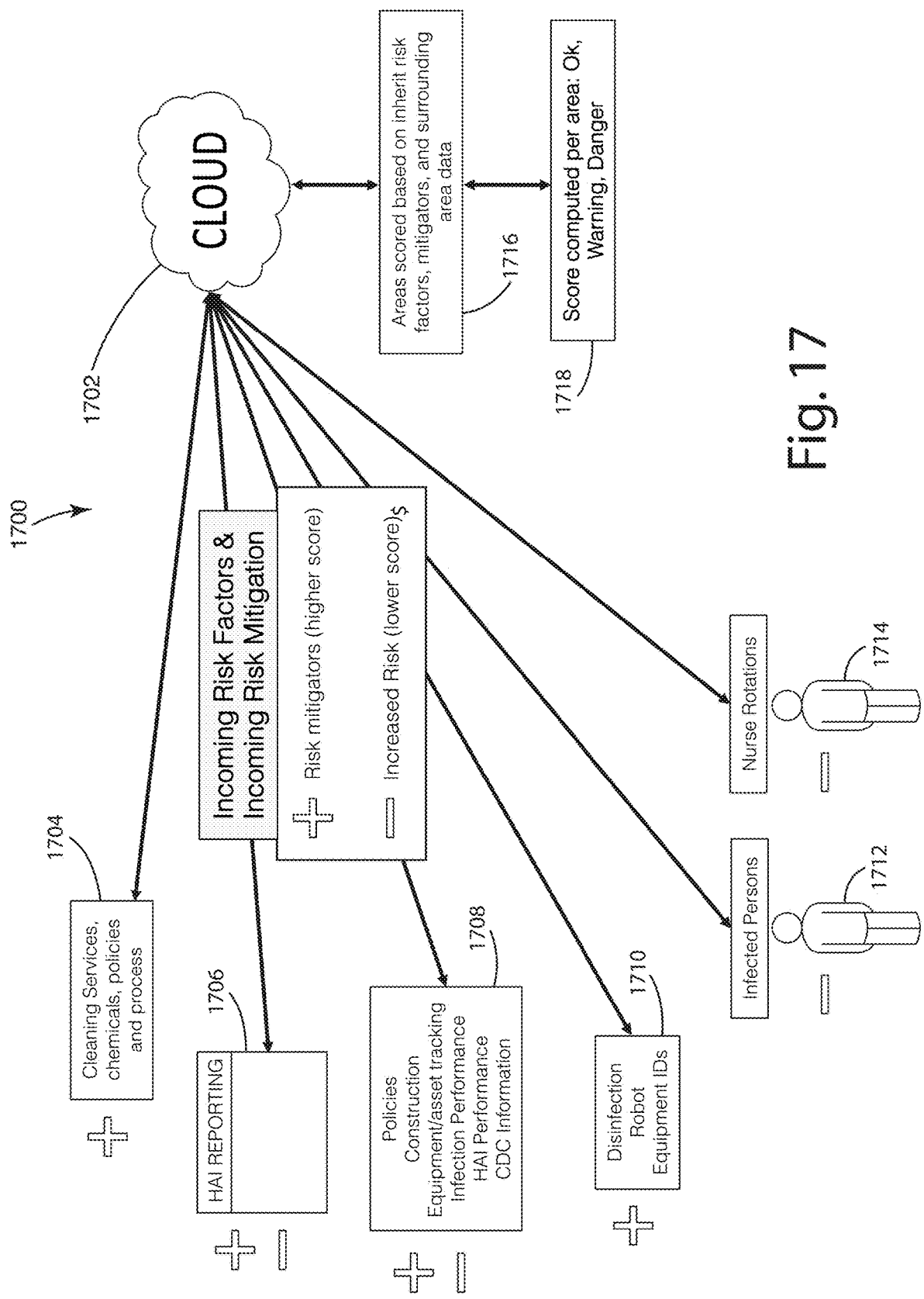
FIG. 17 shows a representative diagram of inputs and outputs for use in connection with an infection related design of experiments.

With regard to FIG. 17, the system can include predicting the effects of incoming risks and incoming actions lowering risk. By using predictive measures to provide countermeasures to incoming risk, the system can address problems. As above, desired state driving can be done and when additional threats to transmission become imminent, policies and tracking policy adherence efforts can be increased. Guiding policies and communicating with staff closely about optimal state and trajectory in real time can reduce risk, educate staff, track mitigation opportunities, and even elevate policies and drive countermeasures based on level of risk. In one example, tracking a number of people moving into a room based on medical records 1706, tracking handwashing, tracking cleaning 1704, tracking terminal cleaning, external equipment, and proximity of infectious persons 1712 can set a baseline to track for optimal performance and calculating a trajectory based on policy compliance from optimal.

By way of example, with regard to FIGS. 18A-B showing optimal and suboptimal states where a low score shows a higher opportunity for infection spread and a high score shows a lower opportunity to spread. A low score (e.g., 1808, 1806, 1816) generally refers to more opportunities for infection to spread such as due to low handwashing compliance, human/equipment in/out weak policies, normal surfaces (as opposed to anti-microbial for example), air movement, equipment tracking, and count of visitors. By way of example, high score (e.g., 1822) generally refers to less opportunities for infection to spread and can be indicative of consistent terminal cleaning schedule, UV disinfection devices installed on high touch surfaces, air disinfection system operational, consistent EVS Cleaning, high handwashing compliance, and reduced equipment/human travel.

Referring to the sub-optimal state illustrated in FIG. 18A, all close proximity rooms may be determined to be at a higher risk due to their infection prevention profile. Countermeasures may be taken beyond what is required to properly mitigate risk, wasting money, time, and resources. Without utilizing incoming data points and risk factors, there is less of an ability to react with direction and speed towards mitigating risk of infection spread. Contrast this with the optimal state shown in FIG. 18B, which adapts to incoming risk factors and data points such as % chance of infection being killed per room, nurse movement, cleaning schedule, etc. This allows for isolation and identifying at risk rooms. When systems reach an optimal state it is possible to compare 'good' vs 'bad' systems and provide advice to improve.

Some embodiments of the present disclosure provide a system and method for predicting pathogen spread risk. For example, a pathogen spread score, which is one example of an infection related score, can be calculated based on a disinfection model that accepts a plurality of different data sources as inputs, as discussed in more detail below with respect to the various examples.

Some embodiments of the present disclosure provide a system and method for reducing pathogen spread. For example, in response to a particular prediction or assessment of pathogen level, such as a pathogen spread score that is indicative of a pathogen level, pathogen transmission probability, pathogen exposure probability, or a combination thereof, a particular countermeasure or set of countermeasures can be automatically initiated or by the system or method. The countermeasure or set of countermeasures can mitigate, reduce, or remediate all or a particular aspect of the pathogen spread. For example, the countermeasure or set of countermeasures may reduce overall pathogen level, for example by automatically increasing UV disinfection device dosage, reducing pathogen transmission probability by increasing frequency of scheduled cleanings of high touch surfaces, or reducing pathogen exposure probability by changing access policies to limit exposure. The countermeasure can be tailored depending on the severity of the pathogen spread score, the trajectory of the pathogen spread score, or depending on any aspect thereof, such as the pathogen level, pathogen transmission probability, or pathogen exposure probability.

FIGS. 2-9 illustrate exemplary flowcharts that show how physical data can be utilized by the disinfection tracking network. A processor can perform the various steps of these flow diagrams to monitor and track various data, which can be utilized in calculating various pathogen related metrics. More specifically, FIGS. 2-9 show some embodiments of how the physical data is processed from occupancy, hand washing, general equipment, environmental services, asset tracking, air treatment, HVAC, and terminal cleaning equipment. The flow charts discuss the various inputs and outputs to the system and how they assist the design of experiments to link outcomes to statistical events in some embodiments. Put another way, these flowcharts illustrate how a processor of the system (e.g., within the disinfection portal or a cloud processing service) utilizes inputs and outputs within the system for tracking statistical probabilities within the statistical design of experiments. Each of the flowcharts will now be discussed in detail.

Figure 2:
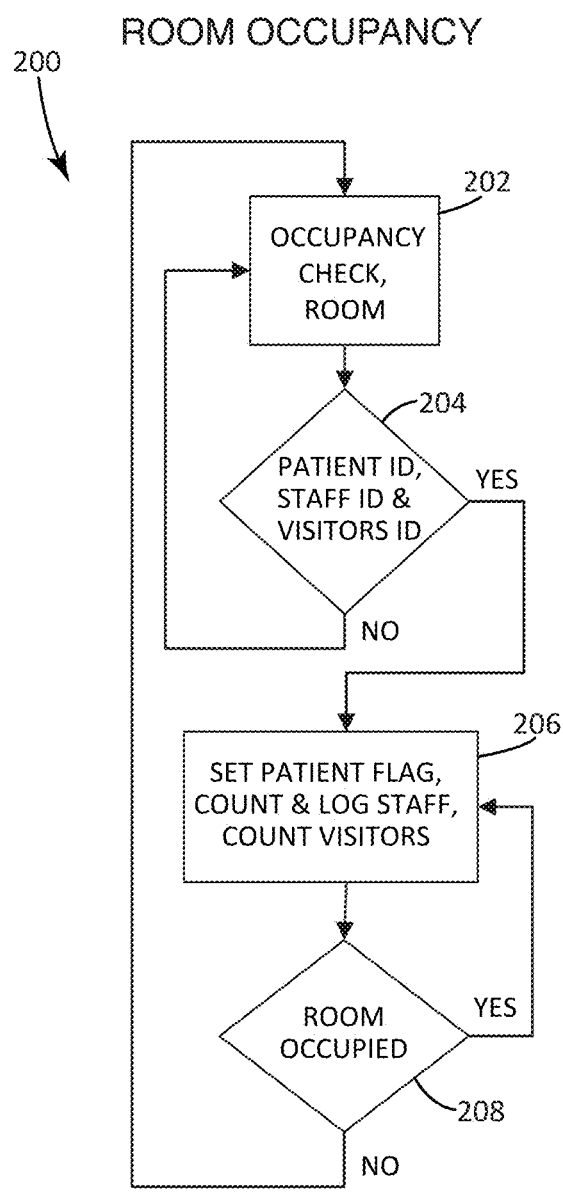
FIGS. 2-9 illustrate representative flowcharts of how different physical data sources are utilized by a disinfection portal to assist the design of experiments to link outcomes to statistical events.

FIG. 2 illustrates an exemplary flowchart for tracking room occupancy of a particular hospital room 200. In this particular example, each room includes sensors that track badges of users as they enter and exit the room. The badge scanner can be passive, or require active input by the user in order to gain entry. As the method begins 202, a particular identifier can be provided for a room, group of rooms, area, or hospital for the query. The ID can be provided using a graphical user interface where the user clicks on a map and the system queries based on the underlying ID associated with that graphical element. The information can also be updated in real-time and shown using a filtered metric that shows a particular user's location over time throughout the hospital facility. The data can also be utilized to show pathing information based on ID and timing events of entry and exit of different points within the hospital. Once the particular room where occupancy is being checked has been identified, the system checks the ID against the IDs associated with the occupancy sensor 204. Patient IDs, staff IDs, and visitor IDs can be saved separately or together in a table, which can be looked up to identify the current occupancy of the room. In some embodiments the occupancy sensor simply records entry and exit events based on ID and provides them to the disinfection portal, which arranges and organizes the data for efficient querying. In response to the occupancy sensor showing any flags being set for patients, staff, or visitors, occupancy count can be noted and updated 206. Further, in this embodiment, the method continues to loop as long as the room is occupied 208 logging patient, staff, and visitor entrance and exits. If a room occupancy sensor senses that all humans have exited the room and there is no occupancy, the sensor can return that value to the system and then wait for a new trigger to begin the loop again—such as a wakeup signal from the occupancy sensor sensing activity or entry in the room. In this way, vast amounts of reliable and real-time occupancy data can be maintained. The occupancy data can be granular or general depending on the application. Further, the sensing is scalable and there may be a few occupancy sensors disposed at key locations within the hospital, or there may be occupancy sensors in nearly all hospital rooms along with other common areas, which can enable high resolution path tracking—particularly useful in identifying areas with higher probability of pathogen transmission risk due to habitation and touching by an infected person. As will be discussed in more detail later, this data can be supplemented by asset tracking data for verification and redundancy.

Figure 3:
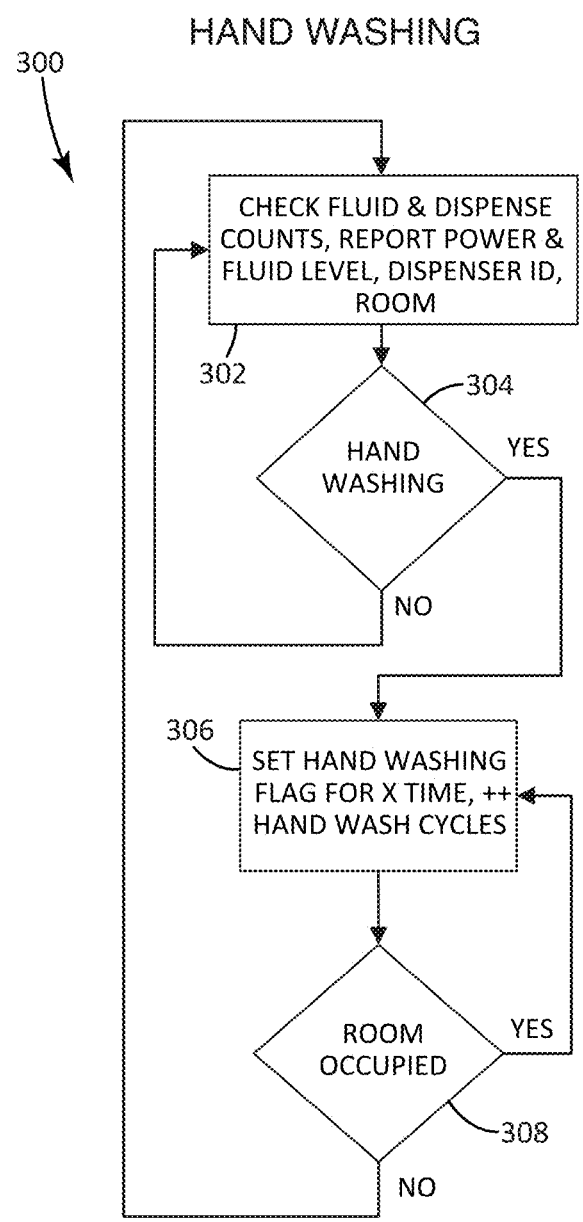

FIG. 3 illustrates a flow chart for processing data from a hand washing sensor 300 together with occupancy data to provide meaningful insights above and beyond the insight available by the data in isolation. The hand washing sensor can return a variety of different metrics depending on the type, model, and configuration of the hand washing unit. Some hand washing sensors are built into the hand washing unit, others are aftermarket that can be installed to sense activation of a third party hand washing unit or sense sink and soap dispenser use. In the current embodiment, the processor accesses fluid and dispense counts, power and fluid level, dispenser ID, and the associated room 302. That is, the hand washing unit can provide one or more pieces of hand washing data, which can include an ID. The ID may be associated in the hand washing unit with a particular room or location, or in many cases, the ID is associated within the disinfection tracking network or within another data source, such as facility data, such that the network tracking system can quickly identify which room the ID of the hand washing unit is associated with. From the various metrics, the processor can trigger for each hand washing event—the event can be determined by the disinfection portal processor by analyzing the data provided by the handwashing data. In some embodiments, a flag or count is directly provided indicating a hand washing event has occurred. If no hand washing event occurred 304, the method can loop and periodically request/poll the sensor or wait for new hand wash data to be pushed to the portal triggering this process. If a hand washing event did occur 304, a hand washing flag can be set for a particular time value based on the data provided 306. That is, the amount of time a user spends washing their hands and the various characteristics of the hand washing event can be characterized according to the provided parameters. Examples can include faucet on time, faucet off time, scrubbing, soap dispensing, and other characteristics. Each hand wash cycle can be incremented and counted. If the room remains occupied 308, the tracking can continue to loop, setting hand washing flags for certain times and tracking hand washing cycles. Once the room is unoccupied, the hand washing routine can revert to waiting for activation or periodic engagement.

In some embodiments, the occupancy data for a bathroom with a hand washing station and sensor are intertwined to gain valuable insights about whether users are washing their hands. The combination of metrics from occupancy sensing and hand washing can be utilized to determine average or general metrics about numbers of users washing their hands after bathroom use, but also to characterize the handwashing technique and timing or statistical information thereof. As an example, an occupancy sensor may have the ability to track a particular user (or type of user, or anonymized user data) entrance and exit times for the bathroom as well as a lack of hand washing activation during those times to effectively determine or at least gain a probable insight into a lack of handwashing after bathroom use. In some embodiments, it may be possible to automate the system to inform the user automatically without having hospital personnel intervene, in order to maintain privacy and save embarrassment. Further, the statistics can be taken at a level of abstraction higher, for example, if 20 people use the bathroom in a given hour, the data can be used to track the number of people that did not utilize the hand washing unit at all, or utilized the hand washing unit in such a way that it did not meet handwashing standards. That information can be statistically analyzed to provide relevant information about the bathroom on the disinfection portal to hospital administrators so that action can be taken. Alternatively, or in addition, signage can be associated with the bathroom to display the average statistics in real time in proximity of the bathroom in order to encourage proper hand washing. Other types of information can also be utilized in increasing the accuracy and resolution of the different types of insights made from combining the hand washing data with occupancy sensor data. For example, different bathroom equipment can provide further insights, such as touch sensors that can sense whether certain surfaces are being touched more than average—which might encourage changing the layout or positioning of certain items within a bathroom to encourage a more disinfectant friendly method of use. Toilet sensors or bidet sensor units can be utilized to inform additional statistics that can be helpful in characterizing the infection related score of the bathroom use. To the extent a bathroom or locker has shower units or other equipment, that equipment may also be connected via the network to the disinfection portal and provide additional data. Furthermore, it should be understood that the model for these characterizations can be improved over time with various types of modeling techniques, such as machine learning and deep machine learning or other artificial intelligence methodologies.

Figures 4, 5:
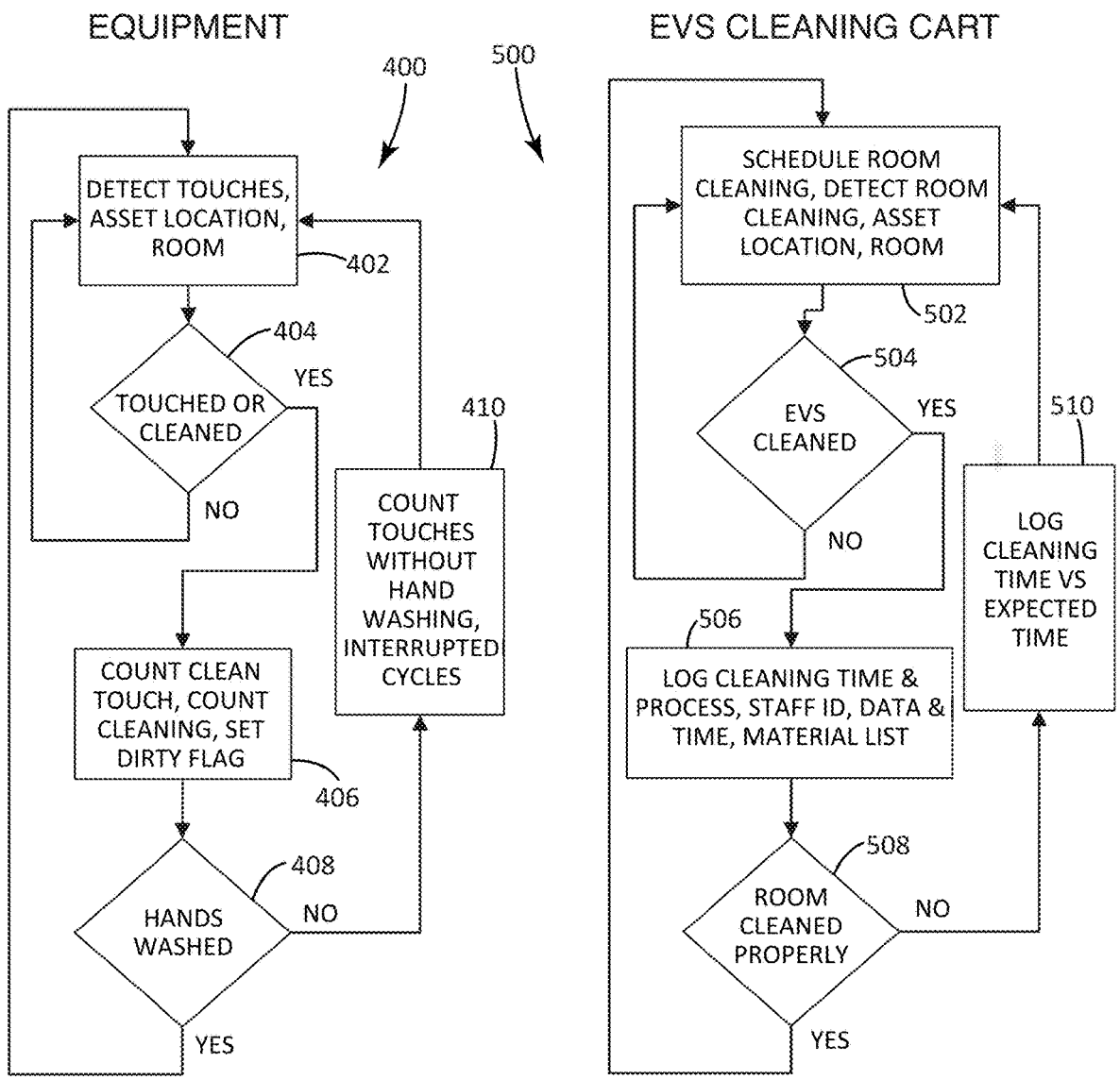

Additional insights can be gained from equipment, for example utilizing the logic flow illustrated in FIG. 4 and denoted as process 400. The equipment can detect touches, asset location, and room location 402, for example, utilizing the ID techniques discussed above in connection with the disinfection portal. The sensors on the equipment can be configured to recognize when the cart has been touched or cleaned 404. For example, an accelerometer, line of sight sensor, or other type of sensor or sensor system including a combination of sensors can be utilized to recognize patterns of activity that provide a high degree of confidence of a touch event, a cleaning event, or in other embodiments, other types of events. If such an event is identified by the pattern of sensor data, the logic flow diagram of this embodiment can count a clean touch, count cleaning, and set a dirty flag. From there, the logic flow can determine whether the users hands have been washed since being exposed to high risk pathogen areas or based on a periodic timer. If no hand washing event is logged within a particular range of time for that user, cart touches without hand washing can be logged, and the number of interrupted cycles can be logged 410 as well, for example, where the cart has a UV disinfection device installed. That is, the equipment may include a UV disinfection device installed thereon, or integral with the equipment, which tracks clean touches of the various equipment surface by a particular user in proximity. The hand washing data can be associated by tracking user ID or occupancy and handwashing data associated by location with the equipment.

FIG. 5 shows methodology for determining whether a hospital room has been cleaned properly 500. The method includes the disinfection portal receiving or accessing data about room cleaning schedules, detecting a room cleaning in progress, asset location tracking of the EVS cart associated with the cleaning, and the particular room location 502. At a high level, the location of the cart and cleaning schedule can be utilized to ensure that the correct room is being cleaned and that the cleaning is associated with the appropriate room. The EVS cart can include various sensors that assist in determining whether EVS cleaned the room appropriately. The sensors on the EVS cart can be processed in concert with other sensor data from sensors located within and about the room. For example, the EVS cart can include sensors indicative of cleaning tool use, such as disinfectant bottles with fluid sensors, towel rack pressure sensors, mop bucket activations, to name a few potential examples. The EVS cart may also include a UV disinfection unit that has its own suite of sensors, which in addition to being able to be used for controlling operation and timing of the UV disinfection equipment, can also provide additional data to the disinfection portal for use in combination with other data to characterize the quality of the EVS room cleaning. For example, the UV disinfection equipment may include features of the UV disinfection equipment described in U.S. Provisional application No. 62/985,976, filed on Mar. 6, 2020 to Baarman et al., entitled "UV DISINFECTION PLATFORM", which was previously incorporated by reference in its entirety. As an example, the UV disinfection equipment can include line of sight sensors, acidometers, gyroscopes, microphones, and passive infrared sensors. These sensors can assist in determining with higher resolution the activity within proximity of the EVS cart and various patterns associated with the sensors. In the depicted logic flowchart of FIG. 5, the processor can log cleaning time and a characterization of the cleaning process, staff ID, date, and time, as well as the material list of the EVS cart at the time of the cleaning. The processor can also assess whether the room was cleaned properly 508. In one embodiment, the proper cleaning assessment is purely based on a comparison of logged cleaning time vs. expected time. If the cleaning time is below an expected cleaning time threshold amount, the room can be flagged as not being cleaned properly 510. Such flagging can also be associated with the room in a graphical user interface so that a new patient is not assigned to the room in the case of a terminal cleaning until the job is done properly, or in the case for a standard cleaning, the job will not be cleared and another cleaning can be scheduled quickly.

Figures 6, 7:
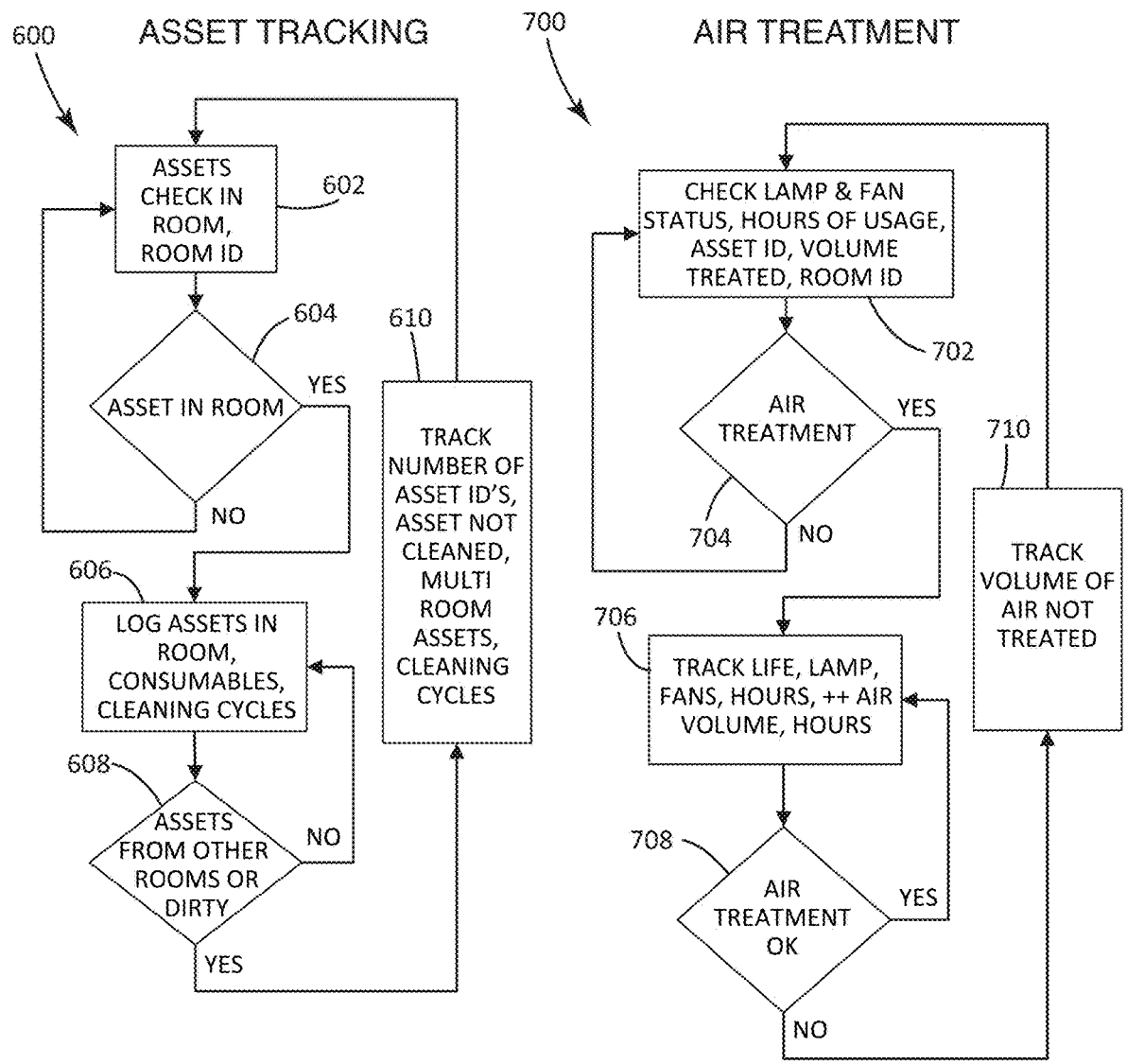

FIG. 6 illustrates a representative flow diagram for determining information about movement of assets from other rooms into a room 600. The method of the depicted embodiment is one that can be continually performed by room 602—other embodiments of asset tracking can be performed on an asset by asset level or group of assets. The assets checked in and associated with the room are checked by virtue of a room ID. If assets are in the room 604, then they are logged, along with consumables and cleaning cycles 606. If assets from other rooms enter the room or if a determination is made that one of the assets in the room has become contaminated 608, then the number of asset IDs, assets that have not been cleaned within a predefined amount of time, multi-room assets, and cleaning cycles are all tracked 610.

Expanding on asset tracking, there are many potential nuances to tracking asset movement throughout a hospital. Assets can include carts, equipment, beds, or essentially any other mobile equipment. In some embodiments, asset tracking can even include nurses, doctors, technicians, other employees or contractors, patients, and visitors that have a particular asset associated with their person whether it be a badge, smartphone, or other token of which movement can be tracked throughout the hospital. The asset tracking methodology can be enhanced over time as additional data is collected about statistical average times with equipment in room and infection rates when paired in rooms with a particular score or score above a particular amount. Physical mobile equipment assets may be treated differently depending on whether they have cleaning or disinfectant procedures associated with them—such as part of routine EVS cleaning, or have UV disinfection devices installed therewith. Different types of assets therefore can be handled differently during infection events. For example, it may be possible to utilize mobile equipment with more disinfection capabilities or higher end features that provide better disinfection outcomes with higher risk areas. For example, carts with higher end anti-microbial surfaces can be deployed to rooms, wings, or areas of the hospital that have a higher average infection related risk score. Such deployments may also be based on trajectory of the risk score.

Many hospitals are beginning to invest more heavily in air treatment systems because they have been shown to increase positive outcomes. Some embodiments of the present disclosure include air treatment systems or at least include receiving data from air treatment systems at the disinfection portal for use in assessing air treatment. In addition, the air treatment data can be utilized to assist in verifying or supplementing to increase accuracy of an infection related score or trajectory. FIG. 7 illustrates one embodiment of a method for collecting certain air treatment data, determining whether the air treatment meets a particular standard, and tracking volume of air not treated 700. Specifically, the processor can receive data indicative of lamp and fan status, hours of usage, asset ID, volume treated, and room ID 702. One exemplary air treatment system that can provide these, and other types of data over a network to a disinfection portal of the present disclosure is described in U.S. Provisional patent application No. 62/956,816 filed on Jan. 3, 2020, entitled "SYSTEM AND METHOD OF DISINFECTION", to Baarman et al., which is herein incorporated by reference in its entirety. If the data collected is indicative of an air treatment event, 704 characteristics about the lamp and fan can be tracked including lamp life, fan life, and active hours 706. In addition, information can be collected about the volume of air treated for that particular treatment system. If the air treatment is deemed in good status, the monitoring can continue 708. If an issue is detected, flags can be set and the system can be notified along with tracking the volume of air not being treated 710, which can factor into the infection related score calculations, such as infection level, spread/transmission rating or probability, and exposure rating or probability scores. The disinfection portal or other cloud system upon analyzing can also issue mitigation instructions, either to increase cleaning efforts by staff in proportion to the risk or for example, by changing the characteristics, such as frequency of dosage or dosage level, of the air treatment systems in adjacent rooms that are more likely to be impacted by the lack of air treatment.

Figures 8, 9:
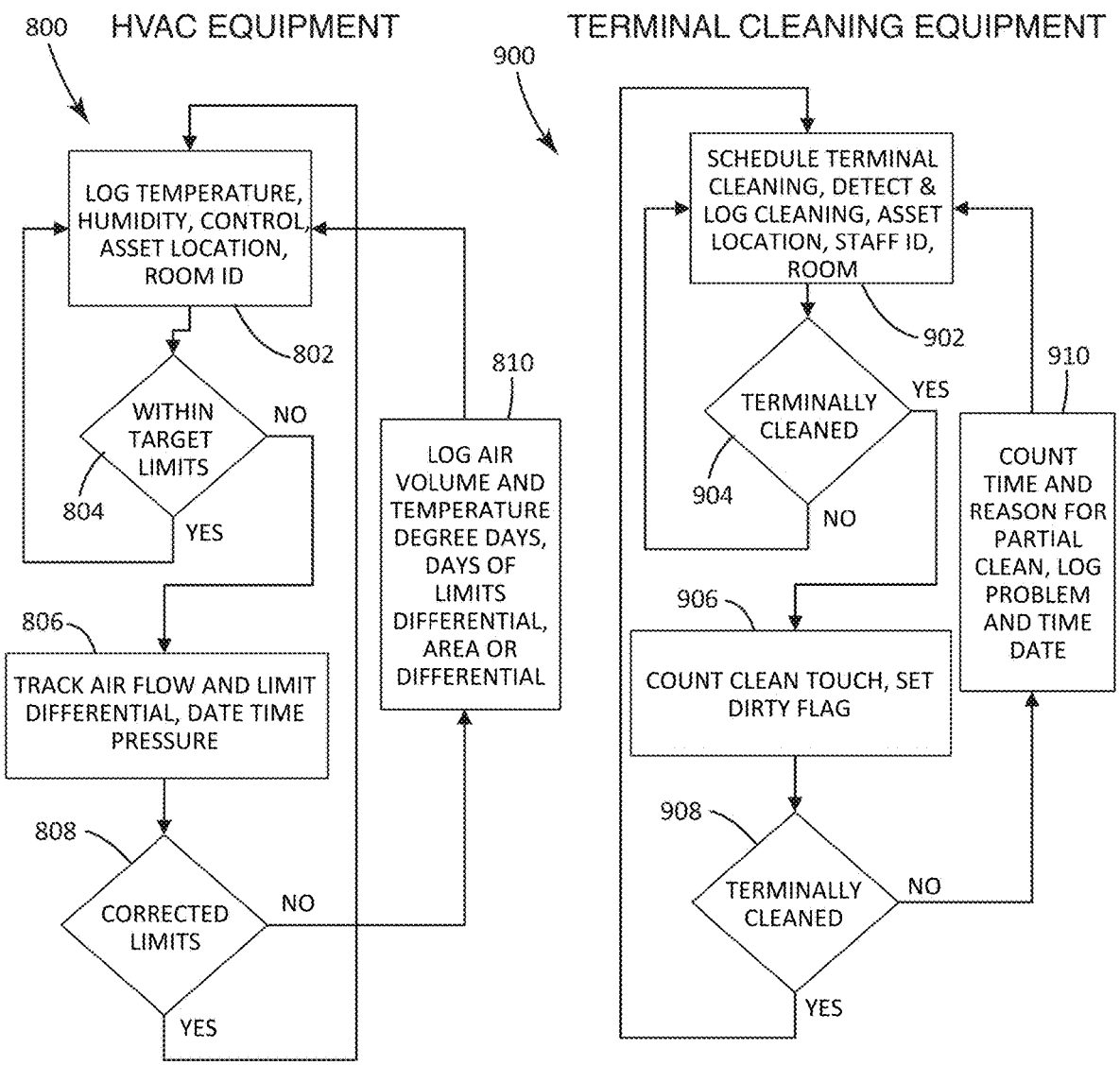

Modern HVAC systems can provide data that when combined with other disinfection portal data can inform meaningful insights and drive better outcomes. One exemplary methodology of using this data is illustrated in FIG. 8 and illustrated in connection with method 800. The method includes logging metrics such as temperature, humidity, control settings, asset location such as a remote thermostat, and room ID 802. The method can assess whether the various metrics in combination or individually fall within a particular target range or below a particular limit 804. If they do, the system loops back and continues to log and monitor the various information—either continuously in real time receiving change updates or by polling periodically, or waiting for pushed data events, just as can be done with almost any of the third party data sources of the present disclosure. If the information is not within the range or below the limit, air flow can be tracked and the differential limited 806. Other metrics such as date, time, and pressure can also be captured to provide more information 808. If the limits are corrected, the process can return to its normal operation 808. However, if the metrics don't return to the proper limits, then even more data can be collected including logging air volume and temperature degree days of limits differential and areas of differential 810.

It is worth noting that at the point where there is a peculiarity or unexpected reading metric or measurement received by the system with almost any of the various methods of the disinfection tracking network, the data sources providing the sub-optimal data can be queried as well as the surrounding data sources. That is, more data can be collected in the case that the system detects a deviation from an expected norm. This additional data can be useful in finding patterns in data that help to explain not only what has actually happened, but why that particular anomaly occurred. Further, the additional data can be helpful in utilizing statistical analysis, design of experiments, and other forms of data analysis, such as machine learning or deep learning to assess potential solutions to prevent the anomaly from occurring again or to correct the situation if it does happen. It is worth noting that the additional data sources queried in this circumstance may not necessarily be the same type of data. For example, if an issue with HVAC equipment is detected, it may be appropriate to query additional data from various sensors and data sources that collect data about items in the vicinity of the room experiencing the issue. Further, although not all data may be provided from the various data sources to the disinfection portal, many of the data sources store raw data or additional data than that which is sent to the disinfection portal, some of the data being stored for at least a short period of time. Accordingly, where events of interest, such as anomalies or infection related scores dip, data sources can be queried for time and data stamped data for not only the window of time where the issue occurred, but also the time leading up to that period—which may include data that explains why the issue occurred. For example, asset tracking data could reveal a cart was moved in front of a duct blocking it.

Terminal cleaning is standard practice in the healthcare industry. Generally, terminally cleaning refers to the more thorough cleaning that is performed on any room once the patient leaves the room in order to prepare that room for the next patient. This can include patient recovery rooms, operating or theater rooms, emergency rooms, consulting rooms, nurseries, sick rooms, lab rooms, or any other room that is subject to terminal cleaning. FIG. 9 illustrates one embodiment of a method of determining if a room has been terminally cleaned 900. The method can include scheduling a terminal cleaning, detecting and logging the cleaning, asset tracking associated with the cleaning, staff ID performing the cleaning, and a room ID associated with the location of the terminal cleaning that is scheduled 902. Using the various information a determination can be made about whether the terminal cleaning occurred 904. If it didn't, it can be rescheduled. If it did, then certain information can be collected during the cleaning that can be used in some embodiments for assessing the quality of cleaning. In addition, clean touches can be counted and a dirty flag set if that count goes above a particular threshold. If the terminal cleaning is completed 908, then the process repeats. However, if the terminal cleaning is interrupted 908, then the reason for the terminal cleaning interruption can be logged. For example, a timer and reason for partial cleaning can be entered by staff along with a date and time stamp 910.

The methodologies described in connection with FIGS. 2-9 are merely exemplary, and it should be understood that there are numerous variations on these different methodologies for tracking infection scores and detecting particular infection related events. These different events can be useful to build a disinfection model. Further, these and other data source combinations can be utilized in executing a statistical analysis such as a set of statistical experiments, such as a design of experiments. Design of experiments generally refers to deliberately changing one or more process variables or factors in order to observe the effect the changes have on one or more response variables. The statistical design of experiments can be an efficient procedure for planning experiments so that the data obtained can be analyzed to yield valid and objective conclusions. The application of the design of experiments methodology is one aspect of the present disclosure. Within the infection context, the DOE begins with determining the objectives of an experiment—for example determining a score indicative of certain infection related events—infection level, infection transmission probabilities for a room, group of rooms or other location, asset or group of assets, or person or group of people, infection exposure probabilities for a room, group of rooms or other location, asset or group of assets, or person or group of people. The disinfection portal can be configured to automatically, semi-automatically, or allow for manual selection of process factors for the experiment. The model of the experiment can begin with various inputs, for example occupancy data and hand washing data, and a particular output response—for example, identifying the number of occupants that exit a bathroom without washing their hands. The experiment can account for uncontrolled factors, such as different hand wash machines, different occupancy sensors, different particular data sets, or other anomalies that might affect the underlying data. The design of experiments can involve the use of an empirical model, such as a linear or quadratic model that relates the various input data to provide an output. Of course, the system can also involve much more complicated models that include complicated cross-product and interaction terms—some of which can be uncovered by application of machine learning in place of design of experiments or as a supplement thereto.

Design of experiments generally begin with a starting data set of inputs. In the current embodiment, the tables below (Tables 1-5) show an exemplary starting data set for an infection design of experiments. Real data is collected about all of these factors based on mitigation strategies and opportunities determining the actual impact of these mitigations. Combining different categories of data provides powerful and meaningful insights. For example, data combined from the following categories can be used to describe and verify the path of a disease outbreak: biological evidence; data indicative of transfer probabilities; data indicative of physical touch tracking; data indicative of physical and asset tracking; and data indicative of a mitigation opportunity data. The data can also be useful for predicting the future path of the outbreak, or which and how much of a particular mitigation will be effective to curtail the outbreak. Examples of the various types of data can include:

TABLE 1

Biological Evidence

Swabbing history
Mediation history/change
Success/proof history
Scientific probabilities of mitigation from peer reviewed papers
Mitigation opportunity impact probabilities
Hospital historical data

TABLE 2

Transfer Probabilities

Room to room equipment
Room history
Room to room staff
Visitors
Touch events
Biological activity
Staff and visitor to room history and path

TABLE 3

Physical Touch Tracking

Equipment touches-who, where
Hand washing
Cleaning events-date and duration

TABLE 3-continued

Physical Touch Tracking

Keyboard touches
Touches by staff-tracking transfer
Biological waste handling
Patient interface

TABLE 4

Physical and Asset Tracking

Room to room equipment
Assets in room
Staff in room-prior history
Hand washing
Visitors

TABLE 5

Mitigation(s) Opportunity

UVC pathogen reduction
Physical cleaning
Room to room equipment cleaning
Room cleaning
Room cleaning-augmentation
Hand cleaning & Glove box
Behavior modifications
Policy modifications
Air treatment
Antimicrobial solutions
Bathroom
Terminal cleaning
Linen handling
Pressure and air flow modifications
Biological waste handling FIG. 10 shows one embodiment of a matrix of data and various data combinations that can be utilized within the disinfection tracking network to monitor and track within the design of experiments to test outcomes statistically. New theories, insights, mitigation strategies, and policy modifications can be objectively tested to detect their impact.

For example, one exemplary hospital (or group of hospitals) can collect the following different types of data for use in executing the design of experiments: EMR data; Internet of Things data; asset tracking data; clinical swabbing and measurement data; hand washing data; room history data; hospital history data; hospital fine data; hospital performance data; surface material data; terminal cleaning data; air disinfection data; cleaning service data; employee tracking data; and touch tracking data. These different data sources can be analyzed through the design of experiments in various combinations to assess infection related mitigations. Examples of infection related mitigations can include identifying a quantifiable relationship between the different data or patterns of data among two or more data sets that are statistically relevant. Other examples of infection related mitigations can include key contributing factors to an infection related score, such as a score that provides a statistically relevant infection level for a room, infection transmission probability for the room as a whole or a particular asset or person in the room (e.g., the probability that the asset or person will transmit a pathogen to another asset or person), and an infection exposure probability for a person or asset entering the room (e.g., the probability that an uncontaminated asset or person will become contaminated by exposure to the room).

Numerous different specific examples are listed in the disinfection network matrix illustrated in FIG. 10 of various design of experiments. For example, in one embodiment, policies can be assessed in terms of EMR data, IOT data, asset tracking data, clinical swabbing and measurement data, hand washing data, terminal cleaning, cleaning service data, employee tracking data, and touch tracking data. The design of experiments can include making a proposed change to the policy and then objectively tracking the results of that policy change relative to the combination of different data sources. FIG. 11 shows a larger disinfection network matrix with additional trackable data within the network that may inform impact by specific statistical changes in these datasets. The table shows data groups with inputs and outputs for the design of experiments.

FIGS. 12-16 show exemplary embodiments and instances of screenshots of a disinfection portal graphical user interface. The user interface includes three main zones: the risk mitigation map zone 1200, the navigation zone 1208, and the notification zone 1206. The risk mitigation map zone 1200 visually depicts scores associated with the different hospital locations. The depicted embodiment shows the scores numerically as well as graphically. Although solid and dashed lines are utilized to depict the scores visually based on thresholds, other forms of visual differentiation can be utilized to convey the risk mitigation and other data. For example, color may be used to visually distinguish different scores on the risk mitigation map. The navigation zone 1200 allows the user to switch between different views available within in the system. The notification zone 1206 shows the status of various devices in the system and can provide access to notifications by the devices.

Figure 12:
FIGS. 12-16 show different embodiments or instances of a disinfection portal user interface.

Referring to FIG. 12, it shows a room cleaning statistical probabilities analysis incorporating touches, hand washing, staff routing, asset routing, events, patient condition, and mitigations. The scores at each room represent that room needs additional augmented cleaning to the standard process. Specifically, room 1204 has a graphical indication of a poor infection related score of 87 indicating it is high risk and needs infection mitigation attention promptly. The other rooms 1202 including the immediately surrounding rooms have low scores (all less than 5 on the 1-100 scale) indicating that the system has determined that the risk of spread to these rooms is low. Changes in scores are determined by a model, for example developed as a result of a design of experiments, such that the various sensor output provided does not match a pattern that is indicative of the high score spreading to adjacent rooms.

Figure 13:
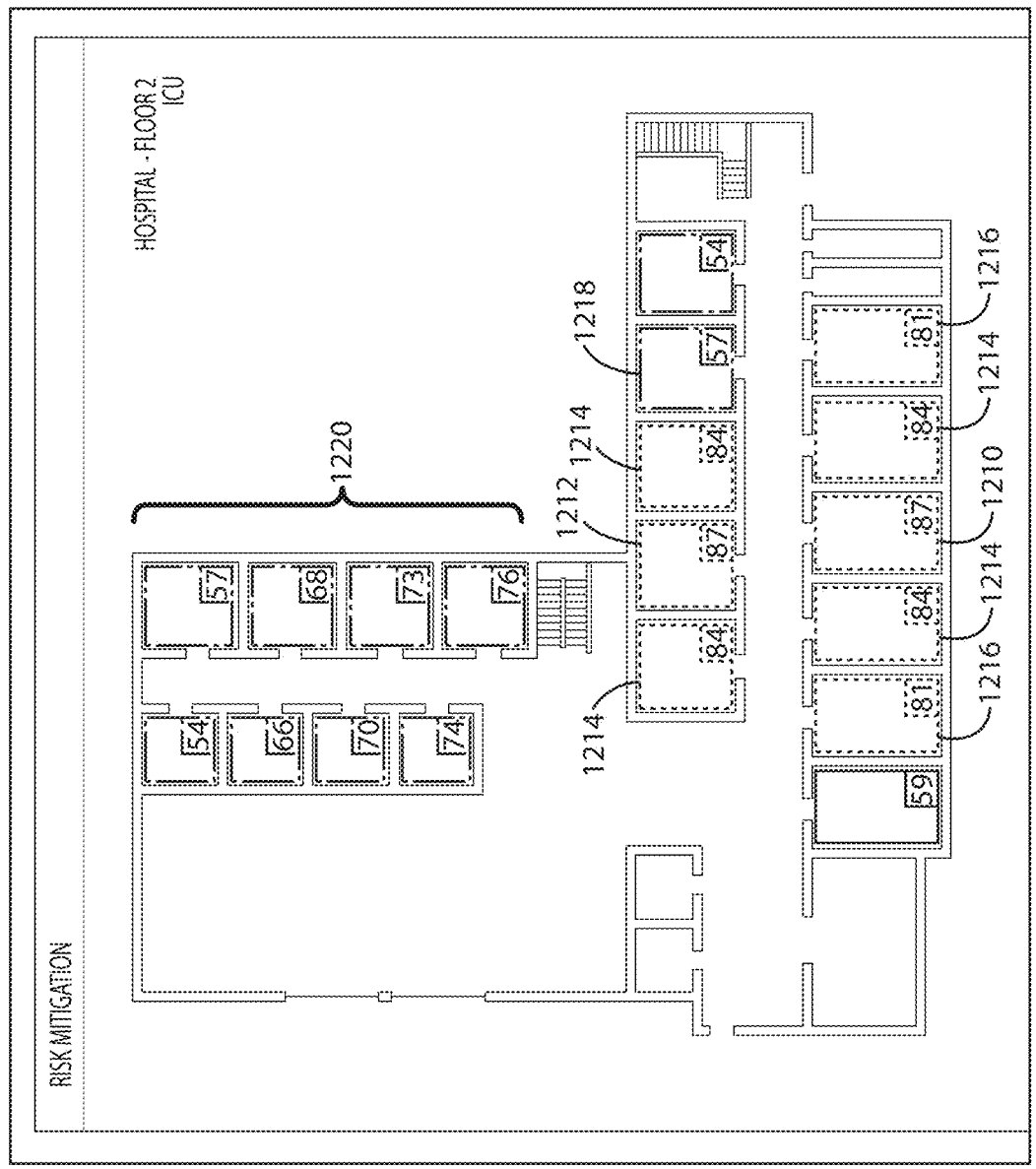

FIG. 13 shows another example of a risk mitigation area of a user interface. This map illustrates levels of augmented process that may be applied as various mitigation levels or opportunities in the design of experiments tailoring the cleaning process and methods to the specific score or levels. The network system seeks to tailor the cleaning specifically to the score always dialing in the success and biological representation of that process. This dashboard shows multiple scores by room. In this embodiment, the initial infection score in 1210 may represent a pathogen spread score (as opposed to a pathogen level score). Further, the scores reflected here can be after the passage of time where enough activity has gone unmitigated that the disinfection portal believes, based on the model and various sensor output, that the pathogen spread risk is rather high, as shown by the scores in the surrounding various rooms. As mentioned above, various different mitigation strategies can be applied depending on the severity of the scores. In a situation such as this, emergency disinfection services may be scheduled for each of the rooms that have a score above a particular threshold (e.g., greater than 80) 1210, 1212, 1214, 1216, while the other rooms that are at risk (such as rooms 1218, 1220) may have restricted access to prevent further exposure. In addition, the system can provide directions such as notice and instructions to increase frequency of hand washing. It may also implement a policy change where visitors cannot enter this portion of the hospital wing. All of this can be done automatically based on various thresholds and limits by the processor of the disinfection portal or the like—triggering different proportional responses based on, for example, individual room scores, or the average or collective scores of groups of rooms.

Figure 14:
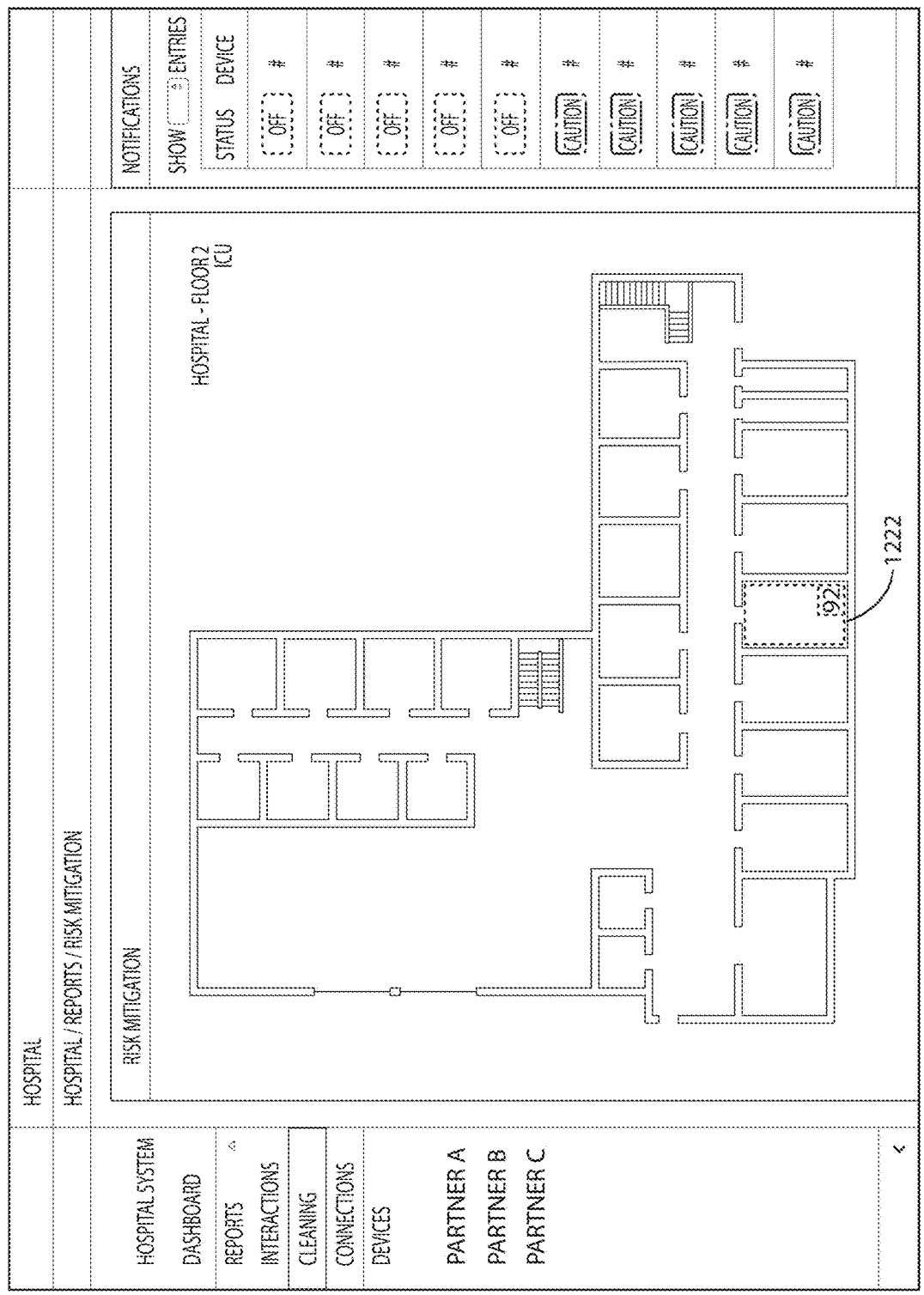

FIG. 14 illustrates a graphical user interface configuration of one embodiment. In this embodiment, room 1222 is shown with an infection risk score of 92. This can represent an interface where the scores are filtered to those above a particular threshold for dealing with emergency threat levels to allow less severe risks to be handled through automation mitigation alone, while more severe risks can be handled by a combination of automated mitigation and service level mitigation by staff.

Figure 15:
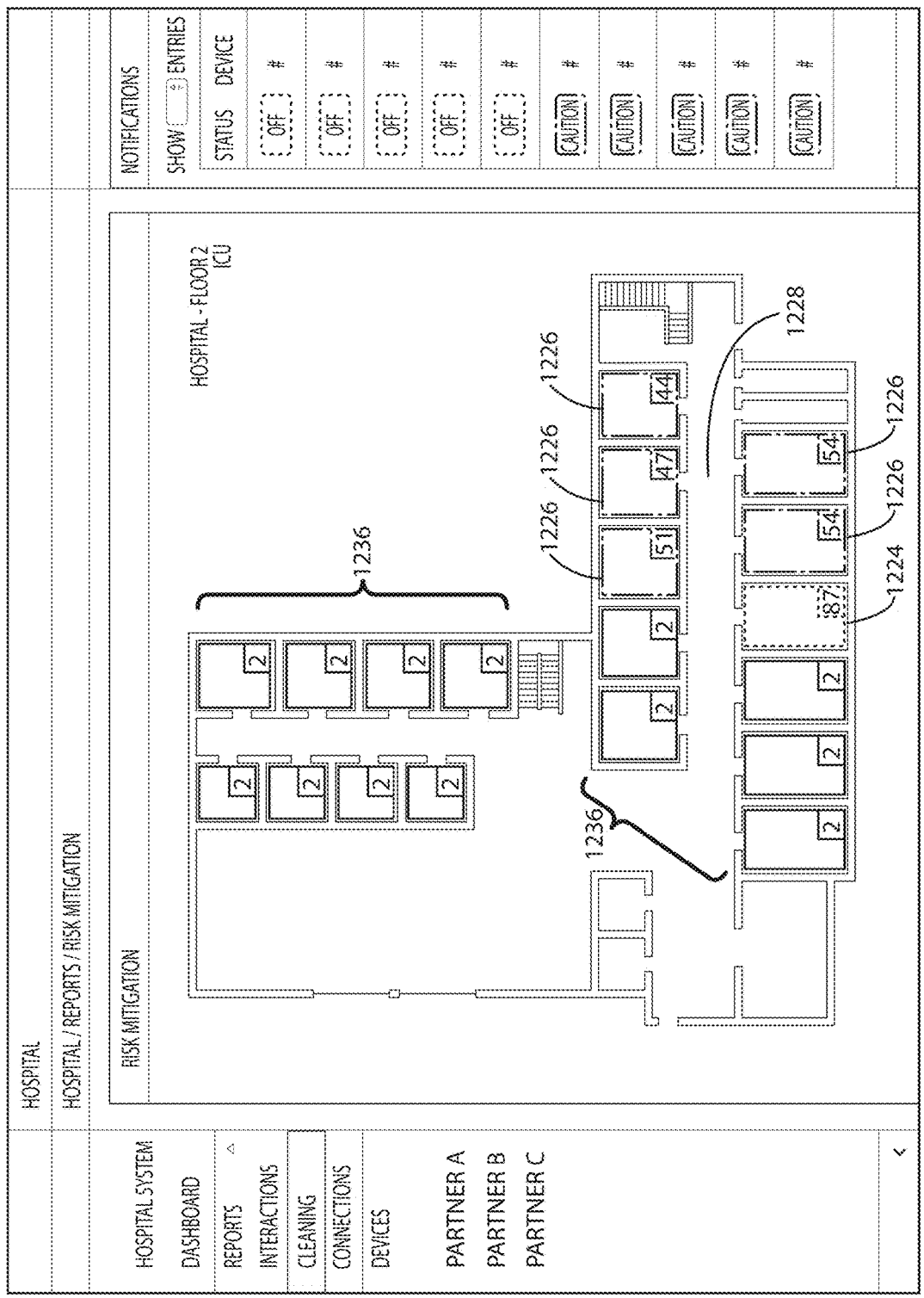

FIG. 15 shows another embodiment where the graphical user interface indicates a high risk area 1224, medium risk areas 1226, and low risk areas 1236. The interface shows the logical mitigation and cleaning strategy by staff coverage and risk probabilities within the design of experiments. The spread risk may indicate the medium risk areas 1226 are higher risk than rooms 1236 because of tracking data showing movement of assets from room 1224 down hallway 1228 toward rooms 1226.

Figure 16:
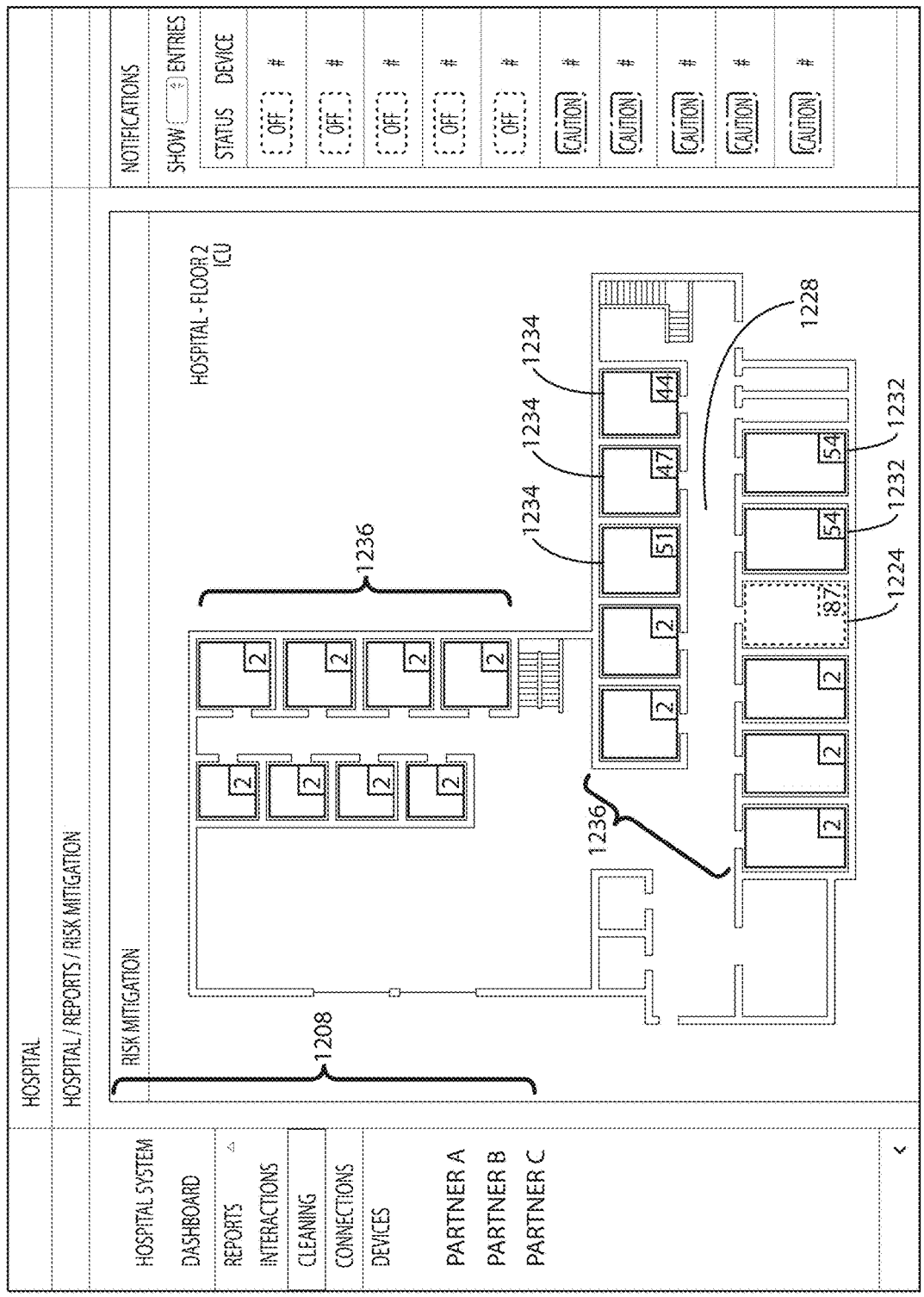

FIG. 16 shows the logical mitigation and cleaning strategy by staff room coverage and risk probabilities within the design of experiments in another embodiment. As opposed to FIG. 10, the elevated risk is reduced as staff members work together to handle the rooms 1234 first. Further, the rooms can be color coded based on thresholds of the score and on trajectories. In the depicted embodiment, rooms 1232 have a score of 54 and rooms 1234 have a score of 2, but they may both be colored yellow (or marked with another indicator), for example due to trajectory of score. That is, the GUI instance shown in the depicted embodiment illustrates the current infection spread score (or risk mitigation score)—if the system predicts that a score trajectory is trending upwards, it can change the color of the room before the score actually changes. This could occur, for example, if a staff member has a high probability of transferring pathogens and moves from the high risk area 1230 to the other rooms 1232, then due to other information about employee-scheduled rounds, they know that a staff member is scheduled to go to rooms 1234, which is why the trajectory is showing the score will increase. The system can attempt to interrupt the staff member to have them wash hands or perform other mitigation tasks, which can reduce the trajectory without ever having the actual risk score go up for rooms 1234. It is worth noting that action requests can be based on sub optimal trajectory and based on a higher trajectory of infection possibility driving higher expectations of policy and procedures. An example would be to increase hand-washing protocols, cleaning policies, human and equipment travel, etc. The network can drive push messages for education to staff and other actions when engaging equipment and going room to room.

FIG. 17 shows a representative diagram of one embodiment of a disinfection tracking network 1700 of the present disclosure. As described in connection with FIG. 1, the system can include a disinfection portal with a processor or access to a cloud processor for analyzing and processing data from a plurality of data sources. Exemplary infrastructure for gathering the inputs and outputs for the design of experiments are depicted in FIG. 17, such as an interface to cleaning services, chemicals, polies, and process 1704, HAI reporting interface 1706, an interface to hospital policies construction information, equipment and asset tracking, infection performance, HAI performance, CDC information 1708, and disinfection robot equipment IDs 1710. The inputs have weighted impacts based on physical events that input to the design of experiments and maintain the risk outputs on room alterations or lack of following policy that changes the impact within the design of experiments. For example, the infected persons known 1712 and nurse rotation data along with other information from the various interfaces 1704, 1706, 1708, 1710 can be fed to the processor in the cloud 1702 where areas can be scored based on risk factors, mitigations, and surrounding area data 1716. Scores can be computed per area 1718 and according to a threshold for color coding (or other visual indicators), which can be applied to a hospital layout map to provide a visual representation of the location and spread of pathogens. As discussed above in more detail in connection with the discussion of optimal vs. sub-optimal state, FIGS. 18A-B show how a visual indication of scores can be applied to a wing of a hospital.

An example of a statistical design of experiments using multiple inputs to determine statistical outputs will now be described. Biological data and physical inputs can enable a level of actual statistical approach to these environments. The disinfection statistical design of experiments for and how elements are taken into consideration statistically. Variations and outcomes can be statistically tracked to accomplish what each pilot or countermeasure contributes statistically. A custom risk percentage can be provided per system. The overall goal of the DOE can vary. In the current embodiment, the goal is to mitigate risk spreading outside of the immediate system by using engineering solutions (UV air disinfection, UV disinfection devices, terminal cleaning, hand washing, and other engineered solutions) even when risks are found via HAI reporting. The DOE can assist in providing a model system so that no matter where infections are discovered/originate, that the overall risk elsewhere stays normalized (under a certain threshold). The DOE can also assist with providing a next best action recommendation, allowing differentiation among different mitigations based on objective statistical experiments. For example, the DOE can recommend increasing surfacide score by a particular percentage, increase air circulation by a certain amount, or add UV disinfection devices in a particular quantity and placement. In short, this example shows a statistical implementation of a disinfection tracking network. differences between rooms/groups to show statistically significant swabbing data points. In this particular example, the next best action learnings include purchasing air disinfection devices versus UV-C low dosage disinfection devices.

Figure 21:
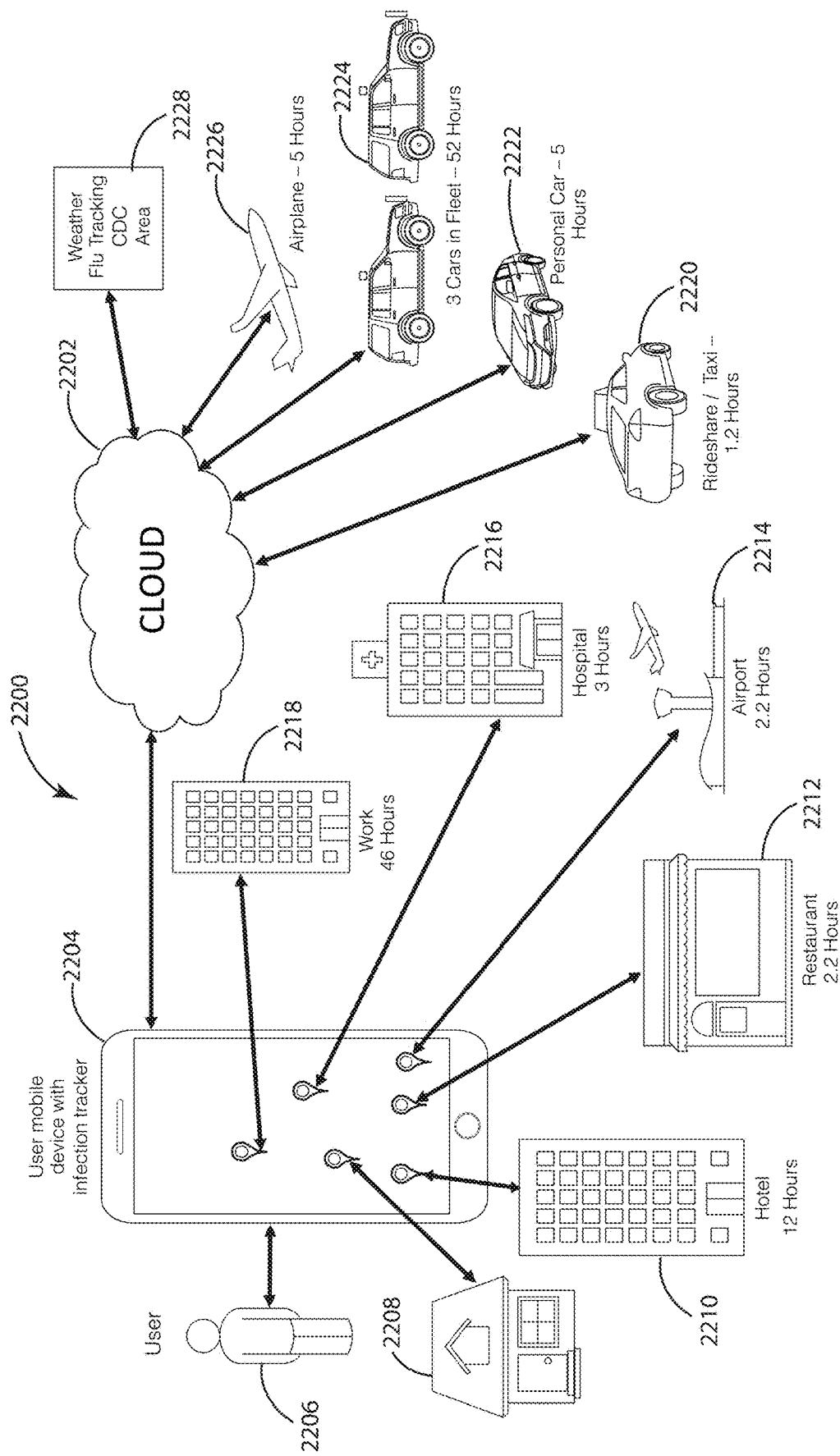
FIG. 21 shows a representative diagram of location and time data collected by one embodiment of a network tracking mobile application.

FIG. 21 shows another aspect of the present disclosure that involves the network tracking health care workers and a present state of health. Tracking exposure in the hospital and exterior from the hospital can be important if we have a health event like the present coronavirus outbreak. This is true of any emergency worker to maximize trackability. Tracking sickness and exposure to others, flights and other environments can be valuable. FIG. 21 illustrates one embodiment of such a tracking system 2200. In the system a disinfection portal, such as the one described in connection with FIG. 1 can be provided within the cloud to analyze and process data received from a user's mobile infection tracker application 2204 as well as from various other third party sources, such as weather/CDC 2228, airplanes 2226, car fleets 2224, personal car 2222, and rideshares or taxi services 2220. This various data from third party sources, together with the data provided from your location services on your mobile device can provide a path on an individual level that is valuable, especially when overlaid with infection data, either the user's or other user infection data and path information.

One aspect of this system is that it can be configured such that each user can own, access, and control their own data. Part of the application can involve only providing anonymized access to data for third party use. Whereas the particular times and geographic information collected by your tracker application that are tied to you can be kept private. For example, a user 2206 may travel between work 2218, hospital 2216, airport 2214, restaurant 2212, hotel 2210, and home 2208. Location and time information can be collected about the user including not only the times and dates of travel to these locations, but the amount of time spent at each location. This data can be valuable data for knowing that someone in a location is sick, because the application can have the user avoid that area. The application provides a simple and effective way to prevent this data anonymously.

Figure 22:
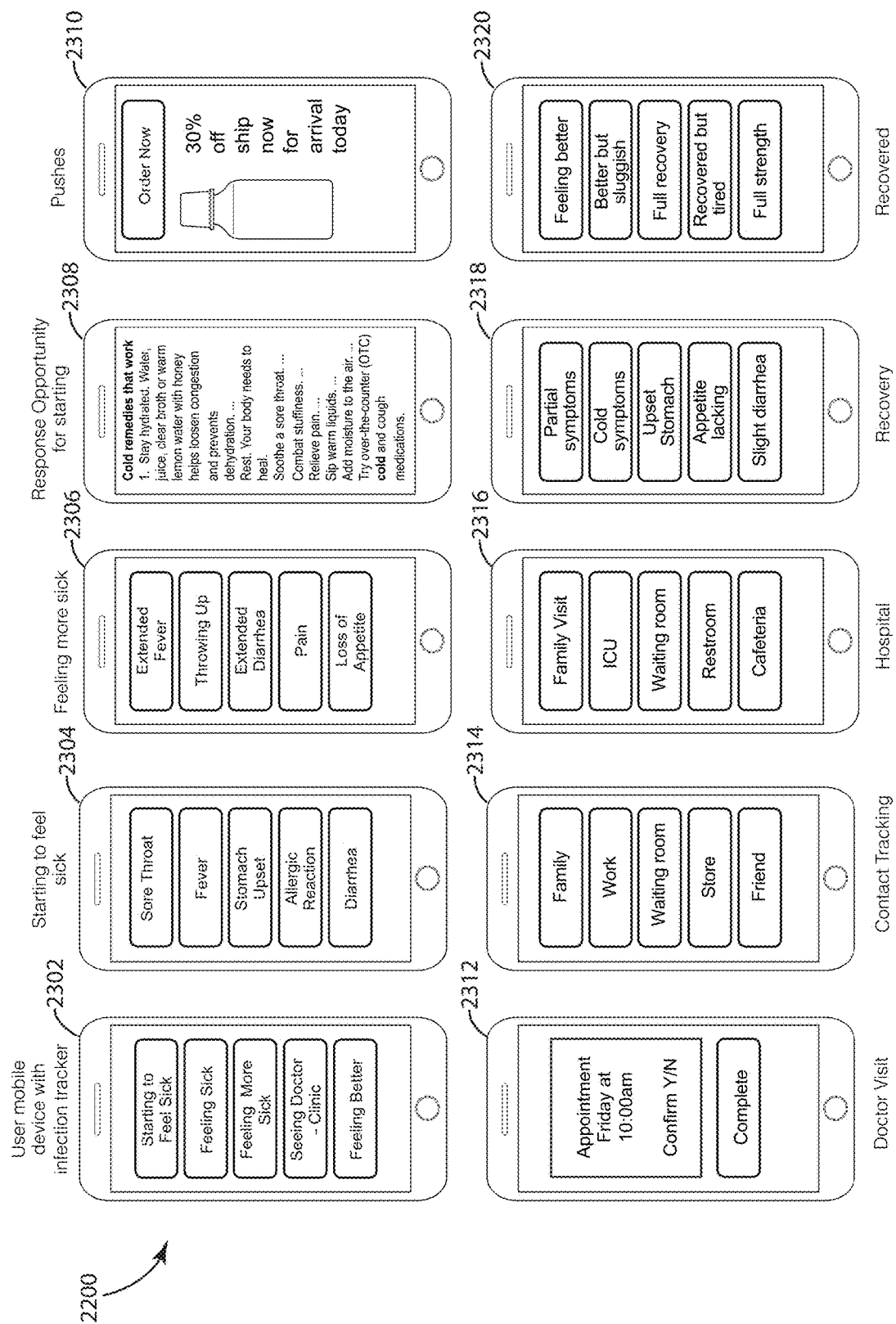
FIG. 22 shows a representative diagram of various interface screenshots of a mobile device with an infection tracker.

FIG. 22 illustrates one embodiment of the mobile application 2200 that gives the user the opportunity for tracking the beginning and ending of an infection and the symptoms, impact and duration enabling doctor inputs, health suggestions and interface opportunities. The application can provide a screen where the user can self-report status 2302, provide additional symptom data 2304, 2306, and the application can respond with potential responses 2308 and product opportunities 2310. The application can also schedule doctor visits or provide access to a doctor over the mobile device communication module 2312. The application can also assist in tracking contacts whereabouts 2314, hospital location 2316, and recovery aspects 2318, 2320. The application can essentially assist in providing a daily/frequent feeling history. It can also log not only when you answered the queries indicating but also inquire and log as to when you self-report starting to become sick—which can be useful to potentially log when and where the infection source may have been. These self-reporting assessments together with the various network of data available from a disinfection portal or similar system, provide a fine grain history of how a user feels. This could be applied at a whole hospital scale, to assess overall feelings over time in an area.

Figure 25:
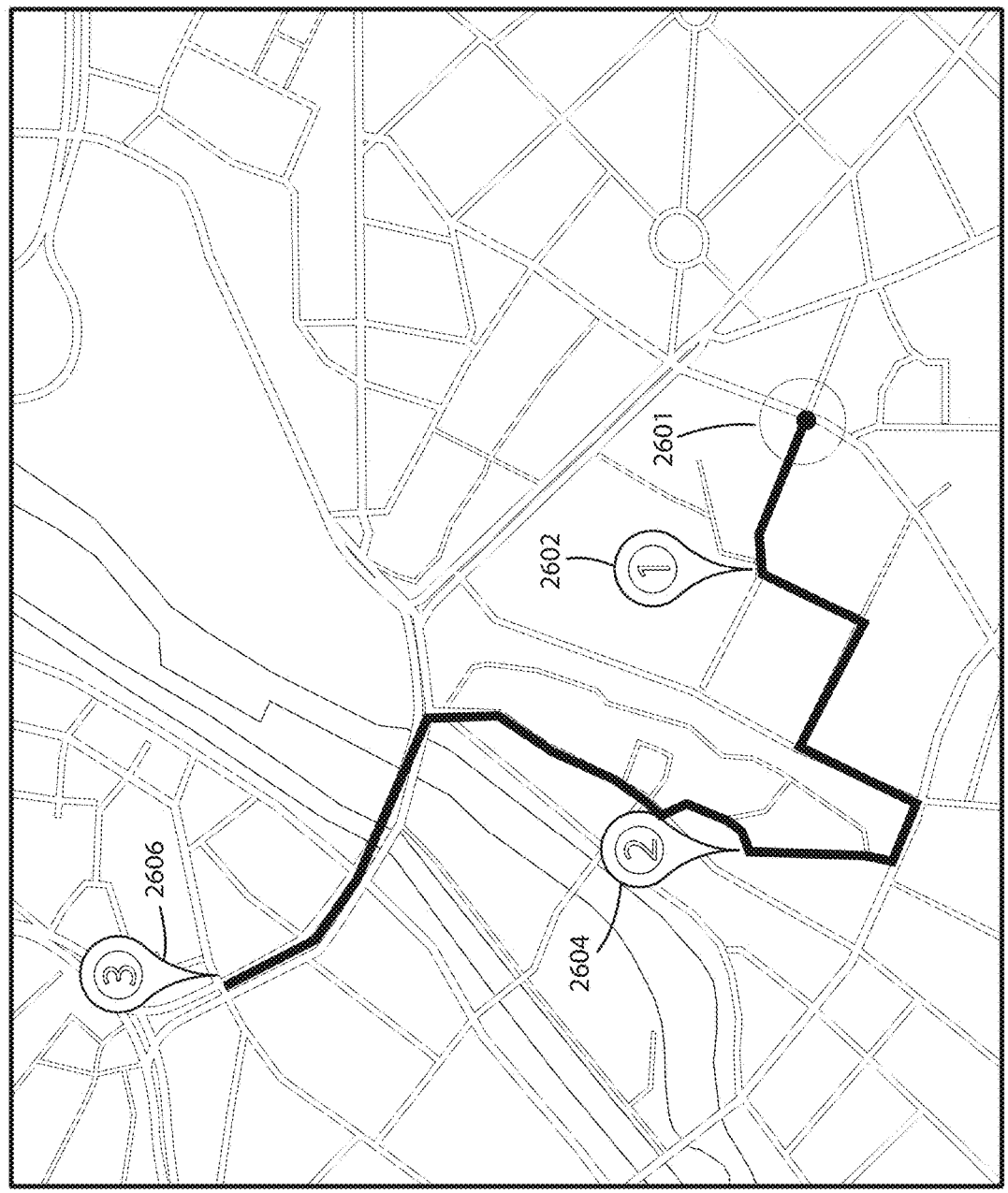
FIG. 25 shows a representative map including user path data, illustrating one embodiment of a pathogen tracking application with integrated pathogen exposure and transmission data melded with pathing data.

Put simply, the mobile tracker application allows tracking of people that are not feeling well and the path of infection with mobile devices. It is an expectation that people occasionally get sick with contagious diseases and will inevitably have contact with others, even if inadvertent. The mobile application of FIG. 23 can track when you start to feel sick, like a sore throat, sick stomach, diarrhea, fever, cough or stuffy nose and tracking follow on sickness for you personally. This data in turn can be used to track your travel and other people you meet with this mobile application. This application and cloud data allows tracking transmission from infected people and exposure to non-infected people. In turn, it becomes a disinfection tool and input into the disinfection network allowing additional research, countermeasures and education. This is a tool for additional design of experiments input to the disinfection network. The application can detect proximity with RSSI BTLE signals and GPS data for participating users. The application can be enabled with sick or enabled to track exposure opportunities. The system can drive transmission countermeasures as well as crowd sourced or doctor, based remedies with expected and trackable outcomes. The tracking of efficacy of these recommendations is followed up by a survey for impact of that recommendation getting to best solutions and outcomes by statistics again. FIG. 25 shows an example of an exposure path.

Figure 23:
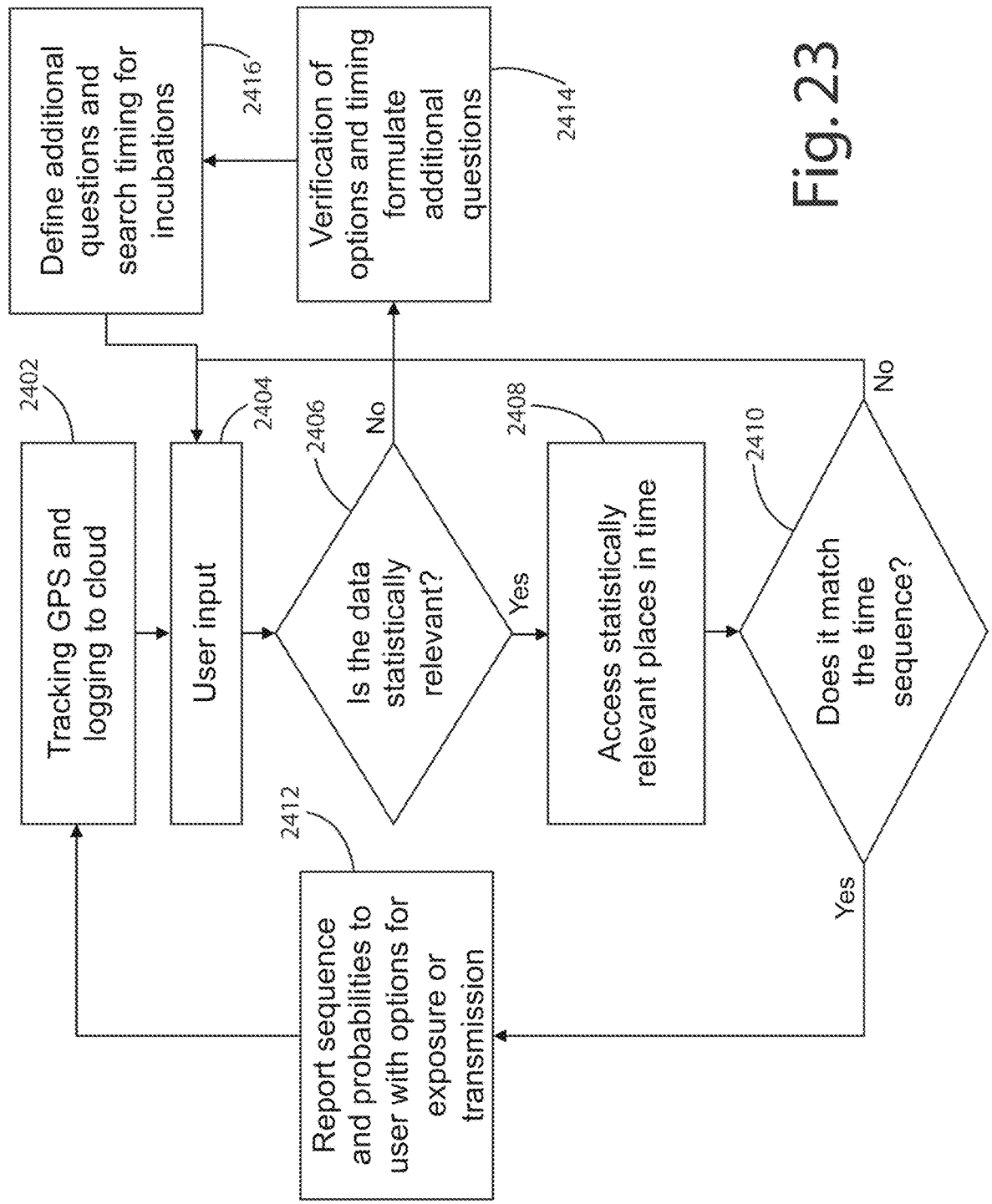
FIG. 23 shows one embodiment of a flowchart for tracking exposure and people with environments using wireless devices and GPS for disease impact and probabilities of spread.

FIG. 23 illustrates a method for tracking exposure and people with environments using wireless devices and GPS for disease impact and probabilities of spread. The methodology of FIG. 24 involves tracking GPS and logging to a cloud system 2402, accepting user input 2404, and deciding whether the data is statistically relevant 2406. If it is, access can be provided to statistically relevant places in time 2408 and the application can decide whether it matches the time sequence 2410. If it does, the sequence and probabilities to user with options for exposure or transmission can be provided 2412. If the data isn't statistically relevant, verification of options and timing can press the user further and ask additional questions 2414. This information can be used to define further questions and search the timing for incubations 2416. If the statistically relevant places in time didn't match the time sequence, then the user can be informed and likely provided a sense of relief.

Figure 24A:
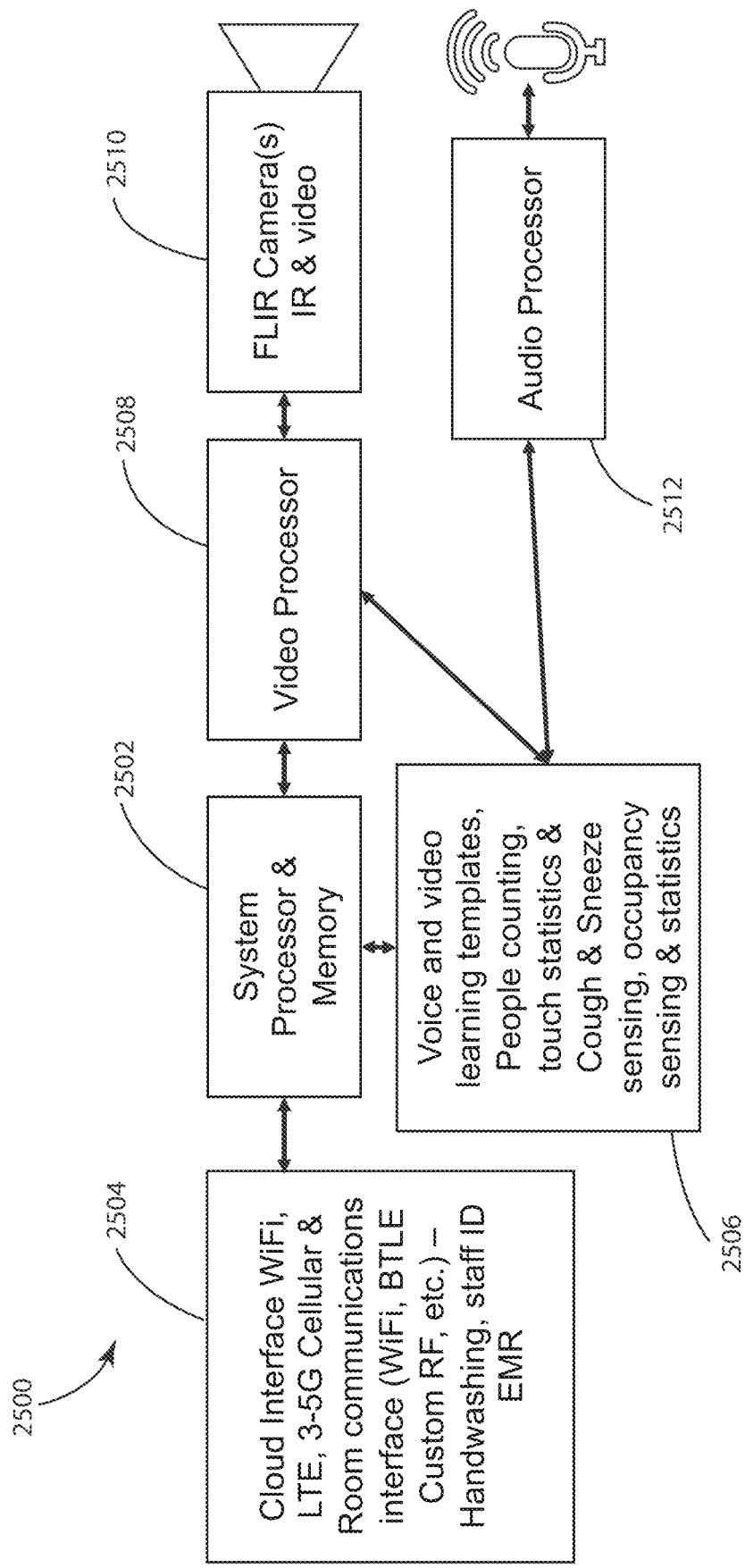
FIG. 24A shows a representative block diagram of one embodiment of a mobile device sickness tracker.
Figure 24B:
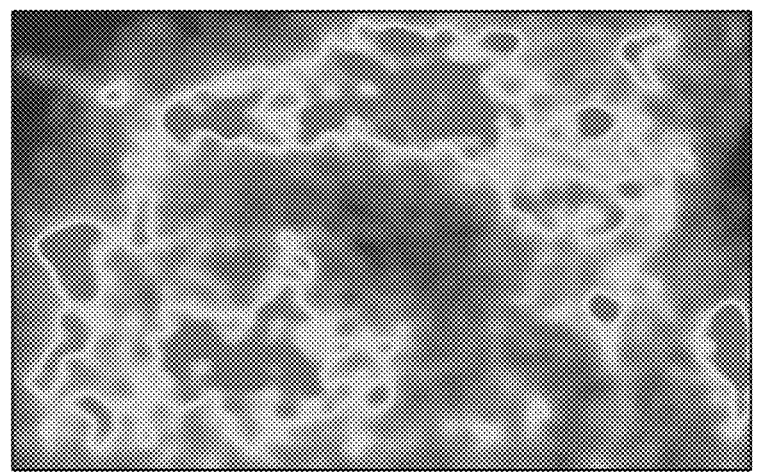
FIGS. 24B-D show representative images of physical inputs collectable by the mobile device sickness tracker of FIG. 24A.
Figure 24C:
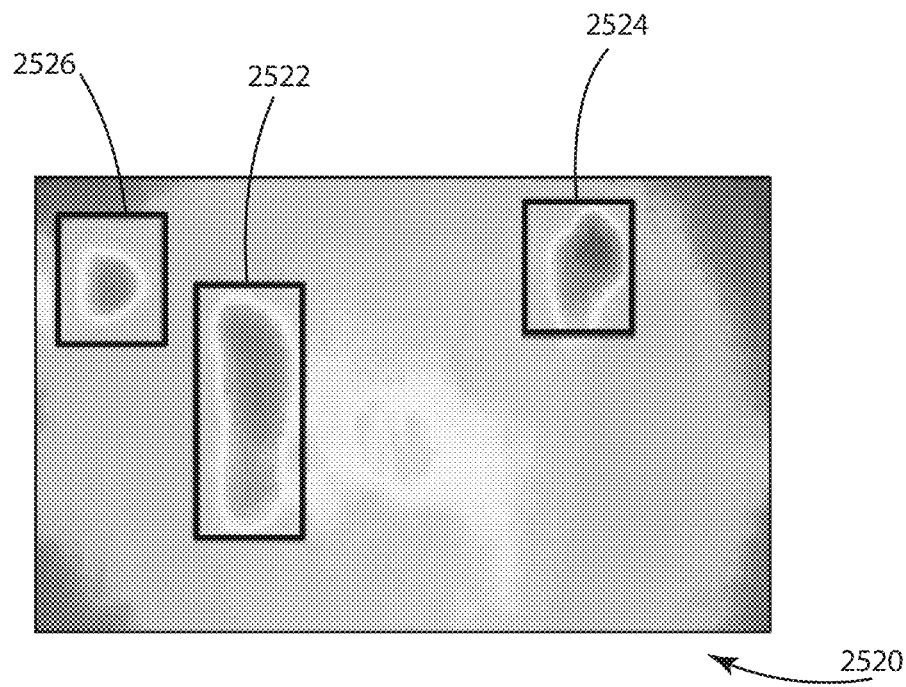
Figure 24D:
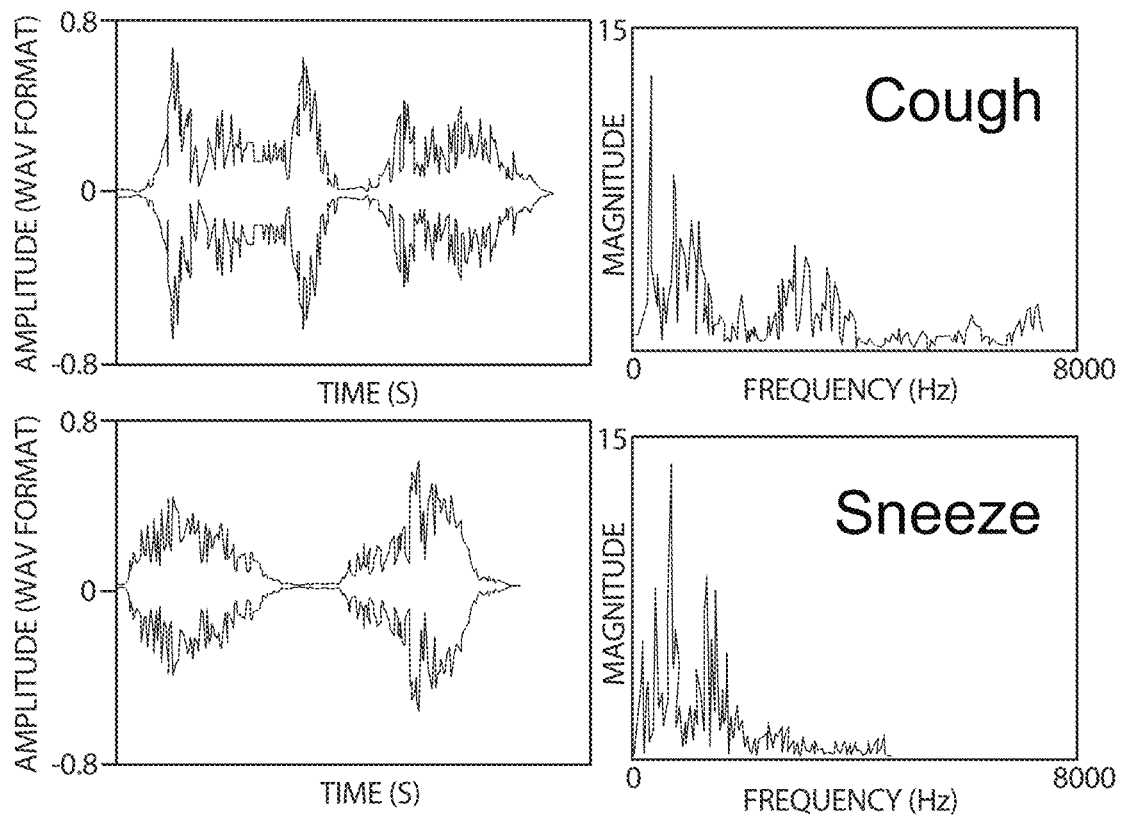

FIG. 24A shows one embodiment of a mobile device sickness tracker and FIGS. 24B-D show several scenarios of how physical inputs can be utilized to define risk to a user and how this is qualified by physical inputs and how that data is captured. Tracking room or vehicle cabin sneezing, coughing and people counting for touches and exposure can impact these exposure and risk scores.

The mobile device tracker 2500 can include a processor 2502 that can communicate using a communication interface 2504. The processor can be connected to voice and video learning templates, people counting, touch statistics & cough & sneeze sensing, occupancy sensing & statistics 2506. The processor can also be or have a connection to a video processor 2508 including an FLIR camera or cameras IR and video 2510. The system may also include an audio sensor and processor 2512. FIG. 24B shows an overhead view of a touch het map 2514. FIG. 24C shows a people counting and tracking image 2520 with the ability to process and identify people 2522, 2524, 2526. FIG. 24D shows how audio data can be used to identify and differentiate through processing coughs and sneezes.

The tracker 2500 is one embodiment of an environmental monitoring system for health evaluation. Using body counting, visitor and staff tracking, touches, movements, coughing and sneezing can be a valuable tool. This information by itself can be an important tool to quantify the health of an environment and changing probabilities based on this information. This information can be used to drive countermeasure suggestions and your personal exposure. This monitoring system includes an imaging system for the purpose of tracking movement, occupancy, body counting and touch patterns. The monitor also has an audio tracking system that recognizes sneezing, coughing tracking intensity and time of these events and counting seconds of activity and intensity as a weighting. This system can also be used as an occupancy detection device for UVC terminal cleaning when nobody is present in room and door is closed. This system may be used in a bathroom, patient room, operating room, other buildings, retail and vehicles. Outcomes may drive interactions like driving air treatment acceleration or countermeasures.

FIG. 25 shows one exemplary instance of an embodiment of a map 2600 that captures exposure and transmission data over physical stops visited. For example, each location 2602, 2604, 2606, when integrated with on the interface can provide information about potential exposure at those locations during the times a non-infected user was present according to the tracking location. As another example, where a user is infected, the data can be useful to show the potential places where the user may have transmitted the infection. For example, the map shows concrete data about time and place of visit. Such data may be helpful to the user for contacting loved ones and warning them about the situation.

While FIG. 25 shows an external map relative to a single user within the context of the mobile tracker application of FIG. 22, this same concept can be utilized at a hospital level where the layout of the hospital can be provided with pathing for individual users overlapping to show exposure and transmission. Hospitals can track nurses and staff and their movements, understanding where they have been and what they could have carried with them. Additionally, this data can factor into any infection related score calculations such that certain events can add a risk to certain rooms after staff have left a low score room, and enter other rooms, thereby lowering the score of that room. The weighting and timing of the score reduction can even by dynamic depending on whether the person or employee has good hygiene practices, or for longer term if they have bad practices or scores.

Figure 26:
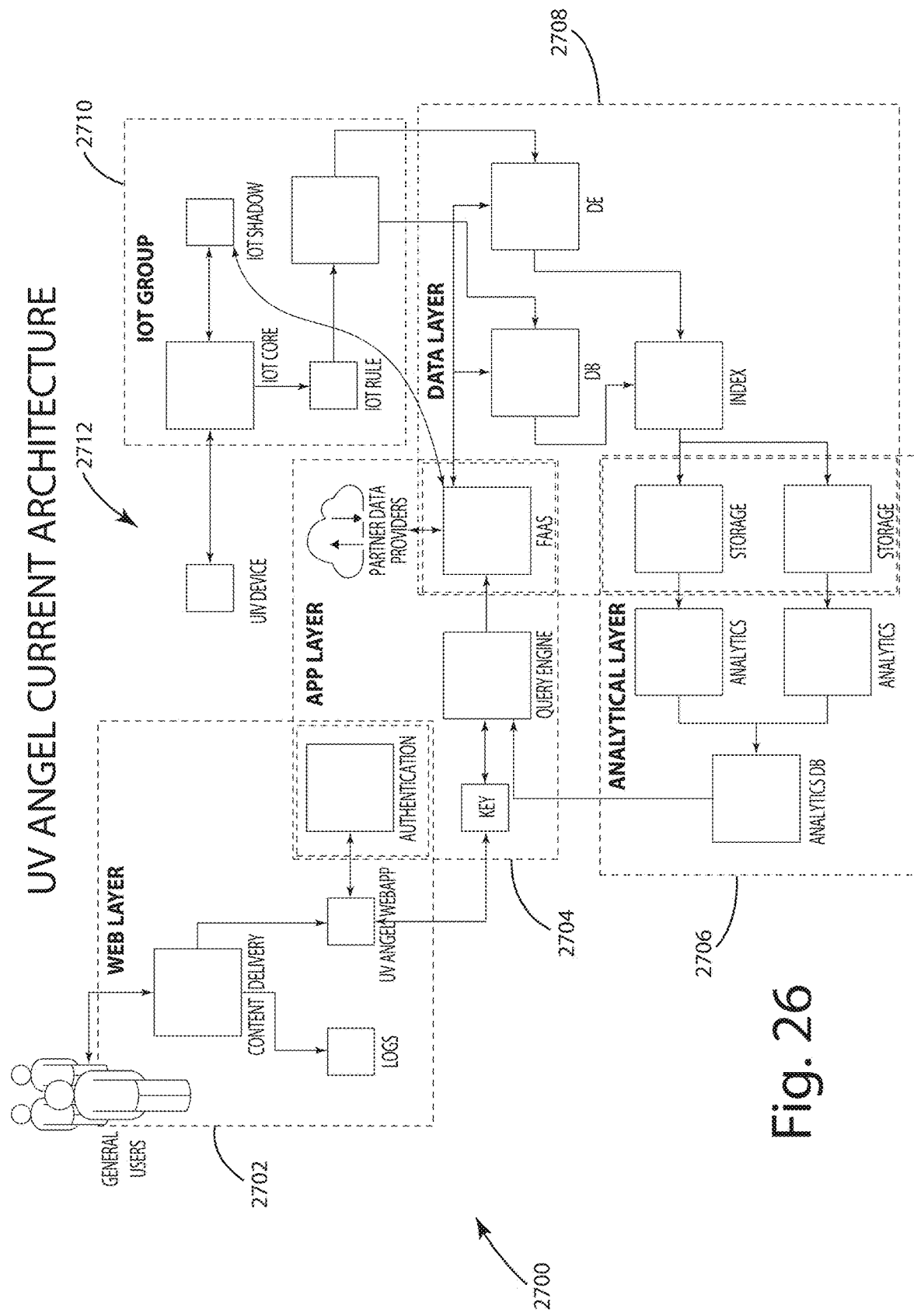
FIG. 26 shows a representative block diagram of one embodiment of cloud architecture for a disinfection portal or disinfection tracking network system.

FIG. 26 shows one embodiment of a disinfection tracking network architecture 2700. The cloud architecture for Internet of Things (IoT) includes cloud data layers, analytical layers, and the mobile application layer with unique ID and security features. In general, the architecture can include a web layer 2702, application layer 2704, analytics layer 2706, data layer 2708, and IOT group 2710, and may include one or more UV disinfection devices 2712.

An exemplary disinfection algorithm for calculating an infection related score will now be described in detail. The disinfection algorithm is, at its heart, a weighted score computation. As data streams and inputs change, the score can be continually recomputed to give an accurate, up to date metric on the overall pathogen spread risk that is relevant to a specific area in a system. The overall score computed can show the assumed pathogen spread risk for a given system. A higher score indicates a high probability of any pathogens leaving the location, and a lower score indicates a lower probability of any pathogen leaving the location. The goal of the score is to give those in control a tangible way of measuring how effective their pathogen spread mitigations are, and what areas of their systems are performing better than others.

The general algorithm can be described as follows. At the single computational group level (e.g., hospital, floor, or hospital system) the sum of all system weights equals 1, where n is the number of data points in a given system. Since the number of data points in a system is variable, the system can store relative weights of data points which show relevance compared to one another—but not overall relevance in a system. Relative weights are relative to each other, and do not need sum to 1, however-given a system that contains 1 to n data points, system weights can be calculated in relation to each other. Weighting is calculated on a per system basis, and percentage weight in relation to other data points is computed as follows:

$$w_i = \frac{\text{relative weight of singular datapoint } i}{\text{sum of relative datapoint weights included in system}} = \frac{r_i}{\sum_{i=1}^{n} r_i}$$

$$\sum_{i=1}^{n} w_i = w_1 + w_2 + \ldots + w_n = 1$$

$w_i = $ system weight of datapoint (↑weight = ↑impact to pathogen spread risk)

In this embodiment, 100% pathogen spread risk is a theoretical maximum calculable risk, and 0% is the theoretical minimum calculable risk, however this percentage is a representation of available data.

System weight of each data point is variable depending on number of data points in the system, and the sum of all system weights will equate to 1 in this embodiment.

2 data points
  Relative Weight A: 7
  Relative Weight B: 4

Total: (Mod $\Sigma_{i=1} r_i$

System weight of $A$: (Mod) $\sim .63_6$
$\phantom{xxxxxxxxxxxxxx}7+4$

System weight of $B$: (Mod) $\sim .364$
$\phantom{xxxxxxxxxxxxxx}7+4$ 4 data points
  Relative Weight A: 7
  Relative Weight B: 4
  Relative Weight C: 4
  Relative Weight D: 9

Total: (Mod $\Sigma_{i=1} r_i$

System weight of $A$: (Mod) $= \sim .291$
$\phantom{xxxxxxxxxxxx}7+4+\overline{4+9}$ System weight of $B$: (Mod) $= \sim .166$
$\phantom{xxxxxxxxxxxx}7+4+\overline{4+9}$ System weight of $C$: (Mod) $= \sim .166$
$\phantom{xxxxxxxxxxxx}7+4+\overline{4+9}$ System weight of $D$: (Mod) $= \sim .375$
$\phantom{xxxxxxxxxxxx}7+4+\overline{4+9}$ The relevance and effectiveness of different hardware systems is backed by many independent studies on pathogen spread risk mitigation. Utilizing comparative analysis of those studies, the system can be configured to arrive at a relevance score for each data point (or lack thereof). In order to choose the correct weight for a data point, a system can periodically or continually re-analyze the data available at any given time.

$$s_i = d_i * w_i$$

$s_i$=weighted score of datapoint i
$d_i$=current datapoint value scaled between 0 (↓ impact), 100 (↑ impact)

The current data point value, scaled between 0 and 100, is computed using all relevant data for a singular data point (example: the average number of UV disinfection device interactions in the last hour). Utilizing metrics from relevant independent studies, the data is scaled between 0 (lowest impact to pathogen spread risk) to 100 (highest impact to pathogen spread risk). The scientific study is utilized to build a scaling function for this data point, of which the output is in the range 0 to 100. (Example: If the study shows that an average of 0 surface interactions in 1 hour shows no increase in pathogen spread in that system, an average of 0 interactions becomes our baseline. If the study shows that an average of 2, 4, and 6 interactions in the last hour contributes more to pathogen spread risk, then our scale becomes 0, 2, 4, 6-linear, maxing out at >=6 interactions over the last X hours).

Accordingly, by example, if our data shows 3 interactions over the last X hours, our datapoint value is 50 (i.e. 50% of this data point's maximum contribution to the system).

For this example, our scaling function is linear $$f(x) = \frac{x}{6} * 100 \text{ on } [0, 6]$$

$$d_i = f(x)_i * 100$$

$d_i$=current datapoint value scaled between 0 (↓ impact), 100 (↑ impact)
$f(x)_i$=scaling function of datapoint i, for input value x Putting everything together, in this embodiment the system can operate according to the following algorithm:
p=Overall System Pathogen Spread Risk Score $$p = \sum_{i=1}^{n} s_i$$

$$p = \sum_{i=1}^{n} d_i * w_i$$

$$p = \sum_{i=1}^{n} (f(x)_i * 100) * w_i$$

$$p = \sum_{i=1}^{n} (f(x)_i * 100) * \frac{r_i}{\sum_{i=1}^{n} r_i}$$

In the following examples, the facilities only collect data on the included data points. Not every disinfection tracking network or system needs to contain all data types, and that system weights are computed from the relative weights the system holds (which are formulated from independent study data analysis).

Scenario A
  Systems included
  Hand Washing (Stored Relative weight: 8)
    System weight: 8/(4+4+8)=0.5
    From study X, as the number of handwashing occurrences increases, the risk decreases exponentially up to 10 occurrences in the last hour. We can calculate the scaling function of handwashing data to be $f(x)=2^{-x}$ of [0, 10]
    Current data point=2 handwashing occurrences
    $f(x)=2^{-2*100=25}$
    0.5*25=12.5

Surface Interactions (Stored Relative weight: 4)
    System weight: 4/(4+4+8)=0.25
    From study Y, as the number of surface interactions increases, the risk increases linearly $$f(x) = \frac{x}{20} \text{ of } [0, 20]$$

Current data point=14 surface interactions $$\frac{14}{20} = 0.7 * 100 = 70$$

0 70*0.25=17.5
  Terminal Cleaning (Stored Relative weight: 4)
    System weight: 4/(4+4+8)=0.25
    From study Z, as the number of terminal cleaning occurrences increases, the risk decreases linearly $$f(x) = 1 - \frac{x}{4} \text{ of } [0, 4]$$

Current data point=3 surface interactions $$1 - \frac{3}{4} = .25 * 100 = 25$$

25*0.25=6.25
  Overall Risk=12.5+17.5+6.25=36.25
Scenario B
  Systems included:
  Hand Washing (Stored Relative weight: 8)
    System weight: 8/(4+4+8)=0.5
    From study X, as the number of handwashing occurrences increases, the risk decreases exponentially up to 10 occurrences in the last hour. We can calculate the scaling function of handwashing data to be $f(x)=2^{-x}$ of [0, 10]
    Current data point=8 handwashing occurrences
    $f(x)=2^{-8*100=0.39}$
    0.5*0.39=0.195
  Surface Interactions (Stored Relative weight: 4)
    System weight: 4/(4+4+8)=0.25
    From study Y, as the number of surface interactions increases, the risk increases linearly $$f(x) = \frac{x}{20} \text{ of } [0, 20]$$

Current data point=2 surface interactions $$\frac{2}{20} = 0.1 * 100 = 10$$

10*0.25=2.5
  Terminal (Stored Relative weight: 4)
    System weight: 4/(4+4+8)=0.25
    From study Z, as the number of terminal cleaning occurrences increases, the risk decreases linearly $$f(x) = 1 - \frac{x}{4} \text{ of } [0, 4]$$

Current data point=4 surface interactions $$1 - \frac{4}{4} = 0 * 100 = 0$$

0*0.25=0
Overall Risk=0.195+2.5+0=2.695
Scenario C
  Systems included:
  Surface Interactions (Stored Relative weight: 4)
    System weight: 4/(4)=1
    From study Y, as the number of surface interactions increases, the risk increases linearly $$f(x) = \frac{x}{20} \text{ of } [0, 20]$$

Current data point=2 surface interactions $$\frac{2}{20} = 0.1 * 100 = 10$$

10*1=10
Overall Risk=10=10
Scenario D
  Systems included:
  Air Particles PPM [Parts per million] (Stored Relative weight: 8)
    System weight: 8/(4+7+8)=0.425
    From study X, as the PPM decreases, the risk decreases linearly. We can calculate the scaling function of handwashing data to be $$f(x) = 1 - \frac{x}{500} \text{ of } [0, 500]$$

Current data point=387 PPM $$f(x) = 1 - \frac{387}{500} = 0.226 * 100 = 22.6$$

0.425*22.6=9.60
Room occupancy (Stored Relative weight: 7)
  System weight: 7/(4+7+8)=0.365
  From study Y, as the number of persons in a room increases, the risk increases linearly $$f(x) = \frac{x}{20} \text{ of } [0, 20]$$

Current data point=2 person in room $$\frac{2}{20} = 0.1 * 100 = 10$$

10*0.365=3.65

Terminal (Stored Relative weight: 4)
  System weight: 4/(4+7+8)=0.210
  From study Z, as the number of terminal cleaning occurrences increases, the risk decreases linearly $$f(x) = 1 - \frac{x}{4} \text{ of } [0, 4]$$

Current data point=1 surface interactions $$1 - \frac{1}{4} = .75 * 100 = 75$$

0 75*0.21=15.75
Overall Risk=9.6+3.65+15.75=29

In the following examples, the facilities only collect data on the included data points. Not every disinfection tracking network or system needs to contain all data types, and that system weights are computed from the relative weights the system holds (which are formulated from independent study data analysis).

As shown in FIGS. 2-9 and discussed above, several examples are illustrated of flow diagrams that can be implemented by systems which can contribute data points into the overall system. Each system can monitor its own data and can constantly update the $d_i$ value which it relates to—therefore constantly updating the overall pathogen spread risk score.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Such components can be physically configured in any suitable manner, such as by mounting them to one or more circuit boards, or arranging them in other manners, whether combined into a single unit or distributed across multiple units. Similarly, steps of a method or process described herein may be embodied directly in hardware, in a software module executed by a processor, or in a combination thereof. A software module may reside in random access memory (RAM), flash memory, read-only memory (ROM), erasable programmable read-only memory (EPROM), electrically erasable programmable read-only memory (EEPROM), registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although particular embodiments have been described of the present invention, it is not intended that such references be construed as limitations upon the scope of this invention except as set forth in the following claims.

The embodiments of the invention in which an exclusive property or privilege is claimed are defined as follows:

1. A mobile infection tracking system, the system comprising:
   a plurality of mobile devices each mobile device having:
      an interface for reporting infectious disease information about a user of the mobile device, wherein infectious disease information is recorded with chronological information in memory as timestamped infectious disease information;
      a position tracking system for tracking position of the mobile device, wherein the position tracking information is recorded with chronological information in memory as timestamped position tracking information;
      a communication system for communicating the timestamped infectious disease information and the timestamped position tracking information over a network; and
   a server configured to receive the timestamped infectious disease information and the timestamped position tracking information over a network from the plurality of mobile devices, wherein the server is configured to estimate infectious disease exposure associated with a user of one of the plurality of mobile devices based on the timestamped position tracking information of the one of the plurality of mobile devices relative to the timestamped position tracking information of the other of the plurality of mobile devices, and the timestamped disease information of the other of the plurality of mobile devices.

2. The mobile infection tracking system of claim 1 wherein the position tracking system of each of the plurality of mobile devices includes a received signal strength indicator (RSSI) for determining strength of signals received from other mobile devices in proximity, wherein the server is configured to estimate infectious disease exposure associated with a user of one of the plurality of mobile devices based, at least in part, on strength of signals received from other mobile devices and the timestamped disease information associated with the other mobile devices.

3. The mobile infection tracking system of claim 1 wherein the position tracking system of each of the plurality of mobile devices includes a global positioning system, wherein the server receives timestamped position information from the plurality of mobile devices and is configured to determine relative positions of the mobile devices based on the timestamped position information.

4. The mobile infection tracking system of claim 1 wherein:
the position tracking system of each of the plurality of mobile devices includes a received signal strength indicator (RSSI) for determining strength of signals received from other mobile devices in proximity and wherein the strength of signals received from other mobile devices in proximity provide position tracking of the mobile device relative to positions of the other mobile devices; and
the position tracking system of each of the plurality of mobile devices includes a global positioning system, wherein the server receives timestamped GPS information from the plurality of mobile devices and the server is configured to determine relative positions of the mobile devices based on the timestamped GPS information.

5. The mobile infection tracking system of claim 1 wherein the timestamped tracked positions include user travel path information, including location information and time information.

6. The mobile infection tracking system of claim 5, wherein the mobile infection tracking system is configured to provide disease exposure estimates, wherein the disease exposure estimates are generated by a disease exposure analysis conducted by the server that assesses whether a user associated with the one of the plurality of mobile devices was exposed to an infectious disease due to co-locating with one or more users having an infectious disease associated with the other mobile devices, at or before the co-location.

7. The mobile infection tracking system of claim 5, wherein the mobile infection tracking system is configured to display graphical and textual information related to probabilities of exposure at particular locations.

8. The mobile infection tracking system of claim 5, wherein the mobile infection tracking system is configured to display graphical and textual information related to infectious disease transmission probabilities associated with attending certain locations.

9. The mobile infection tracking system of claim 5, wherein the mobile infection tracking system is configured to display graphical and textual information related to paths of users associated with certain infectious disease information.

10. The mobile infection tracking system of claim 1, wherein the mobile infection tracking system is configured to trigger an alarm in response to determining a mobile device associated with certain infectious disease information is in proximity.

11. The mobile infection tracking system of claim 1, wherein each mobile device is configured to collect infectious disease transmission data, wherein the infectious disease transmission data weights the infectious disease transmission probabilities.

12. The mobile infection tracking system of claim 5, including a graphical user interface configured to display user travel path information overlaid with infectious disease information.

13. The mobile infection tracking system of claim 1, wherein the interface for reporting infectious disease information includes an interface for at least one self-reporting infectious disease symptoms and an interface for entering an infectious disease diagnosis.

14. The mobile infection tracking system of claim 1, wherein the server is configured to augment the infectious disease exposure estimate based on one or more pathogen factor sensors, each pathogen factor sensor sensing at least one of an infectious disease transmission mitigating factor and an infectious disease transmission exacerbating factor.

15. The mobile infection tracking system of claim 14, wherein the one or more pathogen factor sensors includes a fan status sensor and the infectious disease exposure estimate is modified based on the fan status sensor information, wherein the fan status sensor information includes at least one of active fan hours and air flow rate information.

16. A method of tracking infectious disease exposure using mobile devices, the method comprising:
tracking, with each of a plurality of personal mobile devices, timestamped position information of the plurality of mobile devices over time, the timestamped position information being associated with respective users of the plurality of personal mobile devices;
associating, with a device interface, timestamped infectious disease information associated with at least some of the respective users of the plurality of personal mobile devices;
receiving, at an analysis device, both the timestamped position information from the plurality of mobile devices and the timestamped infectious disease information associated with at least some of the respective users of the plurality of personal mobile devices;
estimating, with the analysis device, infectious disease exposure associated with a user of one of the plurality of mobile devices based on the timestamped position information of the one of the plurality of mobile devices relative to the timestamped position information of the other of the plurality of mobile devices and the timestamped infectious disease information associated with at least some of the respective users of the plurality of personal mobile devices.

17. The method of tracking infectious disease exposure using mobile devices of claim 16, further including:
sensing timestamped infectious disease transmission factors over time; and
augmenting the infectious disease exposure estimating based on the timestamped infectious disease transmission factors.

18. The method of tracking infectious disease exposure using mobile devices of claim 17, wherein the timestamped disease transmission factors include timestamped cleaning information associated with different locations.

19. The method of tracking infectious disease exposure using mobile devices of claim 16, further including:
sensing, with pathogen factor sensors, timestamped infectious disease transmission exacerbating factors over time; and
in response to identifying an event of interest with a device interface, augmenting the infectious disease exposure estimating based on the timestamped infectious disease transmission exacerbating factors.

20. The method of tracking infectious disease exposure using mobile devices of claim 18, wherein the event of interest includes an event of interest time and event of interest location where a discrepancy exists between estimated infectious disease exposure and infectious disease information, and wherein the augmenting includes augmenting the infectious disease exposure estimating based on timestamped HVAC information at the event of interest location leading up to the event of interest time.

* * * * *